United States Patent
De Boer et al.

(10) Patent No.: US 9,073,809 B2
(45) Date of Patent: Jul. 7, 2015

(54) CATALYST SYSTEMS FOR THE CATALYTIC OLIGOMERIZATION OF OLEFINIC MONOMERS

(71) Applicant: Shell Oil Company, Houston, TX (US)

(72) Inventors: Eric Johannes Maria De Boer, Amsterdam (NL); Harry Van Der Heijden, Amsterdam (NL); Quoc An On, Amsterdam (NL); John Smit, Amsterdam (NL); Arie Von Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 40 days.

(21) Appl. No.: 14/133,737

(22) Filed: Dec. 19, 2013

(65) Prior Publication Data

US 2014/0107304 A1    Apr. 17, 2014

Related U.S. Application Data

(62) Division of application No. 13/198,997, filed on Aug. 5, 2011, now Pat. No. 8,637,617, which is a division of application No. 12/859,333, filed on Aug. 19, 2010, now abandoned, which is a division of application No. 11/961,638, filed on Dec. 20, 2007, now Pat. No. 7,803,886.

(30) Foreign Application Priority Data

Dec. 22, 2006 (EP) .................................. 06256571

(51) Int. Cl.
| | | |
|---|---|---|
| C08F 110/02 | (2006.01) | |
| C07C 2/34 | (2006.01) | |
| B01J 31/02 | (2006.01) | |
| B01J 31/18 | (2006.01) | |
| C07F 9/535 | (2006.01) | |
| C07F 9/6571 | (2006.01) | |
| C07F 11/00 | (2006.01) | |

(52) U.S. Cl.
CPC ............... *C07C 2/34* (2013.01); *B01J 31/0265* (2013.01); *B01J 31/189* (2013.01); *B01J 2231/14* (2013.01); *B01J 2231/20* (2013.01); *B01J 2531/62* (2013.01); *B01J 2531/64* (2013.01); *B01J 2531/66* (2013.01); *C07F 9/5355* (2013.01); *C07F 9/6571* (2013.01); *C07F 9/657154* (2013.01); *C07F 11/005* (2013.01); *C08F 110/02* (2013.01)

(58) Field of Classification Search
None
See application file for complete search history.

(56) References Cited

U.S. PATENT DOCUMENTS

| | | | |
|---|---|---|---|
| 5,198,563 | A | 3/1993 | Reagen et al. |
| 5,523,507 | A | 6/1996 | Reagen et al. |
| 5,968,866 | A | 10/1999 | Wu |
| 6,800,702 | B2 | 10/2004 | Wass |
| 7,141,633 | B2 | 11/2006 | Wass |
| 7,273,959 | B2 | 9/2007 | Drent et al. |
| 2005/0113622 | A1 | 5/2005 | Drent et al. |
| 2006/0128910 | A1 | 6/2006 | Blann et al. |
| 2006/0173226 | A1 | 8/2006 | Blann et al. |
| 2006/0211903 | A1 | 9/2006 | Blann et al. |
| 2006/0229480 | A1 | 10/2006 | Blann et al. |
| 2010/0311929 | A1 | 12/2010 | De Boer et al. |
| 2010/0311932 | A1 | 12/2010 | De Boer et al. |
| 2010/0317814 | A1 | 12/2010 | De Boer et al. |

FOREIGN PATENT DOCUMENTS

| | | |
|---|---|---|
| WO | 0204119 | 1/2002 |
| WO | 2004056479 | 7/2004 |
| WO | 2005039758 | 5/2005 |

OTHER PUBLICATIONS

Carter A et al: "High activity ethylene trimerisation catalysts based on diphosphine ligands". Chemical Communications—Chemcom, Royal Society of Chemstry, GB, vol. 2002, No. 8, Mar. 20, 2002, pp. 858-859, XP002277009. ISSN: 1359-7345.
Foss, V.L. et al., "Tetraalkyldiphosphine Imides and the Isomeric Diphosphazanes", M.V. Lomonosov Moscow State University, Zhurnal Ohshchei Khinii, (1984) vol. 54, No. 12, pp. 2386-2399.
Babu, RPK et al., "Unsymmetrical and Symmetrical Diphosphazane Ligands Derived from o-Phenylene Phosphorochloriditte", Heteroatom Chemistry, (1991), vol. 2, No. 4, pp. 477-485.
Babu, RPK et al., "Short-Bite Chiral Diphosphazanes Derived from (S)-a-Methyl Benzyl Amine and Their Pd, Pt and Rh Metal Complexes", Department of Inorganic & Physical Chemistry, Indian Institute of Science, Tetrahedon:Asymmetry (1995), vol. 6, No. 2, pp. 429-438.
Anagho, L.E. et al., "Synthesis and Solid-State Structure of a Metal Complex of a Diphosphinemine", Agnew. Chem. Int. Ed. (2005), vol. 44, pp. 3271-3275.
Raghuraman, K. et al., "Half-Sandwich Cyclopentadienyl Ruthenium Complexes of Achiral and Chiral Diphosphazanes", Department of Inorganic & Physical Chemistry, Indian Institute of Science, J. Chem. Soc., Dalton Trans., (2002), pp. 4289-4295.

*Primary Examiner* — Yun Qian

(57) ABSTRACT

The present invention relates to a ligand and its use in a catalyst for the oligomerization of olefinic monomers, the ligand having the general formula (IV);

$$(R^8)(R^1)P\text{—}N(R^3)\text{—}P(R^4) \tag{IV}$$

2 Claims, No Drawings

CATALYST SYSTEMS FOR THE CATALYTIC OLIGOMERIZATION OF OLEFINIC MONOMERS

CROSS-REFERENCE TO RELATED APPLICATION

This application is a divisional of U.S. application Ser. No. 13/198,997 filed Aug. 5, 2011, which is a divisional of U.S. application Ser. No. 12/859,333 filed Aug. 19, 2010, which is a divisional of U.S. application Ser. No. 11/961,638 filed Dec. 20, 2007, now U.S. Pat. No. 7,803,886, all of which are incorporated herein by reference.

FIELD OF THE INVENTION

The present invention relates to catalyst systems which are useful in the oligomerization of olefinic monomers.

BACKGROUND OF THE INVENTION

The efficient catalytic trimerization or tetramerization of olefinic monomers, such as the trimerization and tetramerization of ethylene to 1-hexene and 1-octene, is an area of great interest for the production of olefinic trimers and tetramers of varying degrees of commercial value. In particular, 1-hexene is a valuable comonomer for linear low-density polyethylene (LLDPE) and 1-octene is valuable as a chemical intermediate in the production of plasticizer alcohols, fatty acids, detergent alcohol and lubrication oil additives as well as a valuable comonomer in the production of polymers such as polyethylene. 1-Hexene and 1-octene can be produced by a conventional transition metal oligomerization process, although the trimerization and tetramerization routes are preferred.

Several different catalytic systems have been disclosed in the art for the trimerization of ethylene to 1-hexene. A number of these catalysts are based on chromium.

U.S. Pat. No. 5,198,563 (Phillips) discloses chromium-based catalysts containing monodentate amine ligands useful for trimerizing olefins.

U.S. Pat. No. 5,968,866 (Phillips) discloses an ethylene oligomerization/trimerization process which uses a catalyst comprising a chromium complex which contains a coordinating asymmetric tridentate phosphane, arsane or stibane ligand and an aluminoxane to produce alpha-olefins which are enriched in 1-hexene.

U.S. Pat. No. 5,523,507 (Phillips) discloses a catalyst based on a chromium source, a 2,5-dimethylpyrrole ligand and an alkyl aluminium activator for use in the trimerization of ethylene to 1-hexene.

Chem. Commun., 2002, 8, 858-859 (BP), discloses chromium complexes of ligands of the type $Ar_2PN(Me)PAr_2$ (Ar=ortho-methoxy-substituted aryl group) as catalysts for the trimerization of ethylene.

U.S. Pat. No. 7,141,633 (BP) discloses a catalyst for the trimerization of olefins comprising a source of chromium, molybdenum or tungsten, a ligand containing at least one phosphorus, arsenic or antimony atom bound to at least one hydrocarbyl or heterohydrocarbyl group having a polar substituent, but excluding the case where all such polar substituents are phosphane, arsane or stibane groups, and optionally an activator. The ligand used in most of the examples is (2-methoxyphenyl)$_2$PN(Me)P(2-methoxyphenyl)$_2$.

Although the catalysts disclosed in the BP documents mentioned above have good selectivity for 1-hexene within the $C_6$ fraction, a relatively high level of products other than the commercially desirable 1-hexene and 1-octene is typically observed.

U.S. Pat. No. 7,273,959 (Shell) discloses a trimerization catalyst composition and a process for the trimerization of olefinic monomers using said catalyst composition.

Catalytic systems for the tetramerization of ethylene to 1-octene have recently been described. A number of these catalysts are based on chromium.

U.S. Published Patent Applications Nos. 2006/0128910, 2006/0173226, 2006/0211903, and 2006/0229480 (Sasol) disclose catalyst compositions and processes for the tetramerization of olefins. The catalyst compositions disclosed comprise a transition metal and a heteroatomic ligand having the general formula $(R)_nA$-B—$C(R)_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group of which at least one R group is substituted with a polar substituent and n and m are determined by the respective valence and oxidation state of A and/or C. The other catalyst compositions disclosed comprise a transition metal and a heteroatomic ligand having the general formula $(R')_nA$-B—$C(R')_m$ where A, B, C, n and m are as defined above, and R' is independently selected from any homo or heterohydrocarbyl group.

U.S. Published Patent Application No. 2006/0128910 (Sasol) discloses the tandem tetramerization and polymerisation of ethylene. Specifically, it discloses a process for polymerising olefins to produce branched polyolefins in the presence of a distinct polymerization catalyst and a distinct tetramerization catalyst, wherein the tetramerization catalyst produces 1-octene in a selectivity greater than 30% and the 1-octene produced is at least partially incorporated into the polyolefin chain.

Although the tetramerization catalysts disclosed in the Sasol documents mentioned above have good selectivity for 1-octene within the $C_8$ fraction, however, only about 70 to 80% wt. of the $C_6$ composition is 1-hexene, with the remaining $C_6$ by-product comprising compounds such as methylcyclopentane and methylenecyclopentane. The presence of these other $C_6$ compositions, which have very little commercial use or value, is highly undesirable from both an economic point of view as well as from a product separation point of view.

Heteroatom Chemistry, volume 2, page 477 discloses the preparation of (phenyl)$_2$P—N(isopropyl)-P=catechol and catechol=P—N(isopropyl)-P=catechol. However there is no disclosure in this document of the use of these compounds in catalyst systems for the trimerization and tetramerization of olefins.

It has now surprisingly been found that the catalyst systems derived from the ligands of the present invention are valuable in providing high levels of both hexene and octene in a process for the simultaneous trimerization and tetramerization of ethylene, with a high selectivity for both 1-hexene and 1-octene within the C6 and C8 fractions, respectively. In addition, the catalyst systems of the present invention have improved activity and allow the trimerization/tetramerization reaction to proceed at industrially attractive process conditions (e.g. elevated temperature and pressure) without fast decay of the catalyst.

SUMMARY OF THE INVENTION

According to a first aspect of the present invention there is provided a ligand having the general formula (I);

$$P(R^4)\text{—}P(R^1)(R^2)\text{=}N(R^3) \qquad (I)$$

wherein:
the $R^1$ group is selected from a hydrocarbyl, substituted hydrocarbyl, heterohydrocarbyl and substituted heterohydrocarbyl group;
the $R^2$ group is selected from hydrocarbyl, substituted hydrocarbyl, heterohydrocarbyl and substituted heterohydrocarbyl groups;
the $R^3$ is selected from hydrogen, a hydrocarbyl group, a substituted hydrocarbyl group, a heterohydrocarbyl group, a substituted heterohydrocarbyl group, a silyl group or derivative thereof;
the $R^4$ group is an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure.

According to a second aspect of the present invention there is provided a ligand having the general formula (II);

$$P(R^1)(R^2)\text{—}P(R^4)\text{=}N(R^3) \qquad (II)$$

wherein:
the $R^1$ group is selected from a hydrocarbyl, substituted hydrocarbyl, heterohydrocarbyl and substituted heterohydrocarbyl group;
the $R^2$ group is selected from a hydrocarbyl, substituted hydrocarbyl, heterohydrocarbyl and substituted heterohydrocarbyl group;
the $R^3$ group is selected from hydrogen, a hydrocarbyl group, a substituted hydrocarbyl group, a heterohydrocarbyl group, a substituted heterohydrocarbyl group, a silyl group or derivative thereof;
the $R^4$ group is an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure.

According to a further aspect of the present invention there is provided a process for the preparation of a ligand of formula (I) or (II) comprising reacting:
i) a compound having the general formula (III);

$$(R^1)(R^2)P\text{—}N(R^3)\text{—}R^5 \qquad (III)$$

wherein:
the $R^1$ group is selected from hydrocarbyl, substituted hydrocarbyl, heterohydrocarbyl and substituted heterohydrocarbyl groups;
the $R^2$ group is selected from hydrocarbyl, substituted hydrocarbyl, heterohydrocarbyl and substituted heterohydrocarbyl groups;
the $R^3$ group is selected from hydrogen, a hydrocarbyl group, a substituted hydrocarbyl group, a heterohydrocarbyl group, a substituted heterohydrocarbyl group, a silyl group or derivative thereof;
the $R^5$ group is selected from hydrogen and a $P(R^6)(R^7)$— group;
the $R^6$ and the $R^7$ groups are independently selected from hydrocarbyl, substituted hydrocarbyl, heterohydrocarbyl and substituted heterohydrocarbyl groups; and
ii) a compound of the formula $X\text{—}P(R^4)$, wherein X is a halide and the $R^4$ group is a group which comprises an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure,
and if the $R^5$ group is hydrogen, a HX-acceptor, preferably at a temperature in the range of from −30 to 200° C.

According to yet a further aspect of the present invention there is provided a ligand system comprising the product formed by reacting
i) a compound having the general formula (III);

$$(R^1)(R^2)P\text{—}N(R^3)\text{—}R^5 \qquad (III)$$

wherein:
the $R^1$ group is selected from hydrocarbyl, substituted hydrocarbyl, heterohydrocarbyl and substituted heterohydrocarbyl groups;
the $R^2$ group is selected from hydrocarbyl, substituted hydrocarbyl, heterohydrocarbyl and substituted heterohydrocarbyl groups;
the $R^3$ group is selected from hydrogen, a hydrocarbyl group, a substituted hydrocarbyl group, a heterohydrocarbyl group, a substituted heterohydrocarbyl group, a silyl group or derivative thereof;
the $R^5$ group is selected from hydrogen and a $P(R^6)(R^7)$— group;
the $R^6$ and the $R^7$ groups are independently selected from hydrocarbyl, substituted hydrocarbyl, heterohydrocarbyl and substituted heterohydrocarbyl groups; and
ii) a compound of the formula $X\text{—}P(R^4)$, wherein X is a halide and the $R^4$ group is a group which comprises an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure,
and if the $R^5$ group is hydrogen, a HX-acceptor, preferably at a temperature in the range of from −30 to 200° C.

According to a further aspect of the present invention there is provided a ligand having the general formula (IV);

$$(R^1)(R^8)P\text{—}N(R^3)\text{—}P(R^4) \qquad (IV)$$

wherein:
the $R^1$ group is selected from a hydrocarbyl, substituted hydrocarbyl, heterohydrocarbyl and substituted heterohydrocarbyl group;
the $R^8$ group is selected from an aromatic or heteroaromatic group which comprise at least one polar substituent group, and optionally one or more non-polar substituent groups;

the $R^3$ group is selected from hydrogen, a hydrocarbyl group, a substituted hydrocarbyl group, a heterohydrocarbyl group, a substituted heterohydrocarbyl group, a silyl group or derivative thereof;

the $R^4$ group is an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure.

According to a further aspect of the present invention there is provided a process for the preparation of a ligand of formula (IV) comprising reacting:

i) a compound having the general formula (V);

$(R^1)(R^8)P\text{—}N(R^3)\text{—}R^5$ (V)

wherein:
the $R^1$ group is selected from hydrocarbyl, substituted hydrocarbyl, heterohydrocarbyl and substituted heterohydrocarbyl groups;
the $R^8$ group is selected from an aromatic or heteroaromatic group which comprise at least one polar substituent group, and optionally one or more non-polar substituent groups;
the $R^3$ is selected from hydrogen, a hydrocarbyl group, a substituted hydrocarbyl group, a heterohydrocarbyl group, a substituted heterohydrocarbyl group, a silyl group or derivative thereof;
the $R^5$ group is selected from hydrogen or a $P(R^6)(R^7)$— group;
the $R^6$ and the $R^7$ groups are independently selected from hydrocarbyl, substituted hydrocarbyl, heterohydrocarbyl and substituted heterohydrocarbyl groups; and ii) a compound of the formula X—$P(R^4)$, wherein X is a halide and the $R^4$ group is a group which comprises an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure,
and
if the $R^5$ group is hydrogen, a HX-acceptor, preferably at a temperature in the range of from −30 to 200° C.

According to the present invention there is further provided a ligand having the general formula (VI);

$(R^9)(R^{10})P\text{—}N(R^3)\text{—}P(R^4)$ (VI)

wherein:
the $R^9$ and $R^{10}$ groups are independently selected from optionally substituted alkyl or heteroalkyl groups;
the $R^3$ group is selected from hydrogen, a hydrocarbyl group, a substituted hydrocarbyl group, a heterohydrocarbyl group, a substituted heterohydrocarbyl group, a silyl group or derivative thereof;
the $R^4$ group is an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure.

According to yet a further aspect of the present invention there is provided a process for the preparation of a ligand of general formula (VI) as described above comprising reacting:

i) a compound having the general formula (VII);

$(R^9)(R^{10})P\text{—}N(R^3)\text{—}R^5$ (VII)

wherein:
the $R^9$ and $R^{10}$ groups are independently selected from optionally substituted alkyl or heteroalkyl groups;
the $R^3$ group is selected from hydrogen, a hydrocarbyl group, a substituted hydrocarbyl group, a heterohydrocarbyl group, a substituted heterohydrocarbyl group, a silyl group or derivative thereof;
the $R^5$ group is selected from hydrogen or a $P(R^6)(R^7)$— group;
the $R^6$ and the $R^7$ groups are independently selected from hydrocarbyl, substituted hydrocarbyl, heterohydrocarbyl and substituted heterohydrocarbyl groups; and ii) a compound of the formula X—$P(R^4)$, wherein X is a halide and the $R^4$ group is a group which comprises an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure,
and if the $R^5$ group is hydrogen, an HX-acceptor, preferably at a temperature in the range of from −30 to 200° C.

According to a further aspect of the present invention there is provided a catalyst system comprising the product formed by combining:
  a) a source of chromium, molybdenum or tungsten;
  b) one or more ligands as described herein and;
  c) a cocatalyst.

According to a further aspect of the present invention there is provided a catalyst system comprising the product formed by combining:
  a) a source of chromium, molybdenum or tungsten;
  b) a ligand system as described herein and;
  c) a cocatalyst.

According to yet a further aspect of the present invention there is provided a process for the oligomerisation of olefinic monomers, wherein the process comprises contacting at least one olefinic monomer with a catalyst system described herein.

DETAILED DESCRIPTION OF THE INVENTION

As used herein, the term "trimerization" means the catalytic trimerization of an olefinic monomer to give a product composition enriched in the compound derived from the reaction of three of said olefinic monomers. The term trimerization includes the cases wherein all the olefinic monomers in the feed stream are identical as well as the cases wherein the feed stream contains two or more different olefinic monomers.

In particular, the term "trimerization" when used in relation to the trimerization of ethylene means the trimerization of ethylene to form a $C_6$ alkene, especially 1-hexene.

The term "trimerization selectivity" when used in relation to the trimerization of ethylene to 1-hexene means the amount of $C_6$ fraction formed within the product composition.

The term "1-hexene selectivity" when used in relation to the trimerization of ethylene to 1-hexene means the amount of 1-hexene formed within the $C_6$ fraction of the product composition. The overall yield of 1-hexene in the trimerization of ethylene is the product of the "trimerization selectivity" multiplied by the "1-hexene selectivity".

The term "tetramerization" means the catalytic tetramerization of an olefinic monomer to give a product composition enriched in the compound derived from the reaction of four of said olefinic monomers. The term tetramerization includes the cases wherein all the olefinic monomers in the feed stream are identical as well as the cases wherein the feed stream contains two or more different olefinic monomers.

In particularly, the term "tetramerization" when used in relation to the tetramerization of ethylene means the tetramerization of ethylene to form a $C_8$ alkene, especially 1-octene.

The term "tetramerization selectivity" when used in relation to the tetramerization of ethylene to 1-octene means the amount of $C_8$ fraction formed within the product composition.

The term "1-octene selectivity" when used in relation to the tetramerization of ethylene to 1-octene means the amount of 1-octene formed within the $C_8$ fraction of the product composition. The overall yield of 1-octene in the tetramerization of ethylene is the product of the "tetramerization selectivity" multiplied by the "1-octene selectivity".

One aspect of the present invention relates to ligands having the general formulae (I), (II), (IV) and (VI):

  (I)

  (II)

  (IV)

  (VI)

wherein $R^1$, $R^2$, $R^3$, $R^4$, $R^8$, $R^9$ and $R^{10}$ are as defined above.

While not wishing to be limited by theory, it is thought that in the presence of an activated metal component (a), e.g. activated chromium, an equilibrium exists between ligands of the P—P=N type and ligands of the P—N—P type. For example:

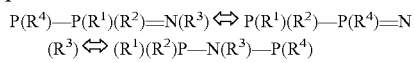

The term "hydrocarbyl" as used herein in relation to the $R^1$-$R^{10}$ groups refers to a group only containing carbon and hydrogen atoms. The hydrocarbyl group may be a saturated or unsaturated, linear, branched or cyclic. If the hydrocarbyl is cyclic, the cyclic group may be an aromatic or non-aromatic group. Unless otherwise stated, the preferred hydrocarbyl groups for use herein are those containing from 1 to 20 carbon atoms.

The term "substituted hydrocarbyl" as used herein in relation to the $R^1$-$R^{10}$ groups refers to hydrocarbyl groups which are substituted with one or more substituents defined hereinbelow.

The term "heterohydrocarbyl" as used herein refers to a hydrocarbyl group wherein one or more of the carbon atoms is replaced by a heteroatom, such as Si, S, N or O. Included within this definition are heteraromatic rings, i.e. wherein one or more carbon atom within the ring structure of an aromatic ring is replaced by a heteroatom.

The term "substituted heterohydrocarbyl" as used herein refers to heterohydrocarbyl groups which are substituted with one or more substituents, defined hereinbelow.

The term "aromatic" as used herein, refers to a monocyclic or polycyclic aromatic ring having from 5 to 14 ring atoms. Examples of polycyclic aromatic groups include biphenyl, binaphthyl, naphthyl and anthracenyl. Unless otherwise stated, the preferred aromatic groups are monocyclic or polycyclic aromatic rings having from 5 to 10 ring atoms. More preferred aromatic groups are monocyclic aromatic rings containing 6 carbon atoms. A most preferred aromatic group is a phenyl group.

The term "heteroaromatic" as used herein, refers to a monocyclic or polycyclic, heteroaromatic ring having from 5 to 14 ring atoms, containing from 1 to 3 heteroatoms selected from N, O and S in the ring, with the remaining ring atoms being carbon. Preferably, the heteroaromatic groups are monocyclic heteroaromatic rings, more preferably monocyclic heteroaromatic groups having from 5 to 10 ring atoms, most preferably from 5 to 6 carbon atoms.

The term "substituted aromatic" as used herein means that the aromatic group may be substituted with one or more substituents defined hereinbelow.

The term "substituted heteroaromatic" as used herein means that the aromatic group may be substituted with one or more substituents defined hereinbelow.

Suitable substituent groups for use in the present invention can contain carbon atoms and/or heteroatoms. The substituents may be either polar or non-polar.

Polar is defined by IUPAC as an entity with a permanent electric dipole moment. Therefore, as used herein, the term "polar substituent" means a substituent group which incorporates a permanent electric dipole moment.

IUPAC defines non-polar as an entity without a permanent electric dipole moment. Therefore, as used herein, the term "non-polar substituent" means a substituent group which does not incorporate a permanent electric dipole moment.

Suitable substituents include hydrocarbyl and heterohydrocarbyl groups, which may be straight-chain or branched, saturated or unsaturated, aromatic or non-aromatic. Non-limiting examples of suitable aromatic substituents include monocyclic and polycyclic aromatic and heteroaromatic groups, preferably aromatic groups having from 5 to 10 atoms in the ring, examples of such groups include phenyl and $C_1$-$C_4$ alkyl substituted phenyl groups. Non-limiting examples of suitable non-aromatic hydrocarbyl substituents include linear or branched alkyl or cycloalkyl groups, preferably having from 1 to 10 carbon atoms, more preferably 1 to 4 carbon atoms. Non-limiting examples of suitable non-aromatic heterohydrocarbyl substituents include linear or branched alkoxy, alkoxyalkyl, alkylsulphonyl, alkylthioalkyl, alkylamino, alkylsilyl and heterocyclic groups.

Other suitable substituent groups include halides such as chloride, bromide and iodide, thiol, —OH, $A^1$-O—, —S-$A^1$, —CO-$A^1$, —N$A^1A^2$, —CO—N$A^1A^2$ in which $A^1$ and $A^2$, independently, are non-aromatic hydrocarbyl or heterohydrocarbyl groups, preferably having from 1 to 10 carbon atoms, more preferably 1 to 4 carbon atoms, e.g. methyl, ethyl, propyl and isopropyl.

Preferred substituent groups are hydrocarbyl groups, heterohydrocarbyl groups, and halides, in particularly hydrocarbyl groups.

The $R^1$, $R^2$, $R^6$ and $R^7$ groups are independently selected from hydrocarbyl, substituted hydrocarbyl, heterohydrocarbyl and substituted heterohydrocarbyl groups.

Examples of suitable $R^1$, $R^2$, $R^6$ and $R^7$ groups include optionally substituted benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl groups.

The $R^1$, $R^2$, $R^6$ and $R^7$ groups are preferably independently selected from optionally substituted aromatic and optionally substituted heteroaromatic groups, more preferably optionally substituted aromatic groups, especially optionally substituted phenyl.

In one embodiment of the present invention, the $R^1$ and $R^2$ groups are independently selected from an aromatic or heteroaromatic group, especially phenyl, which comprises at least one polar substituent group, and optionally one or more non-polar substituents.

In another embodiment of the present invention, the $R^1$ and $R^2$ groups are independently selected from an unsubstituted aromatic or heteroaromatic group, preferably an unsubstituted aromatic group, especially phenyl.

In yet another embodiment, $R^1$ is selected from an aromatic or heteroaromatic group, especially phenyl, which comprises at least one polar substituent group, and optionally one or more non-polar substituents, and $R^2$ is selected from an unsubstituted aromatic or heteroaromatic group, especially phenyl.

Suitable non-polar substituent groups include hydrocarbyl substituent groups which do not contain heteroatoms.

Examples of suitable non-polar substituents include methyl, ethyl, propyl, butyl, isopropyl, isobutyl, tert-butyl, pentyl, hexyl, cyclopentyl, 2-methylcyclohexyl, cyclohexyl, cyclopentadienyl, phenyl, bi-phenyl, naphthyl, tolyl, xylyl, mesityl, ethenyl, propenyl and benzyl groups, or the like.

Preferred non-polar substituent groups include alkyl groups, in particularly $C_1$-$C_4$ alkyl groups such as methyl, ethyl, propyl, isopropyl, butyl, and isobutyl groups.

Suitable polar substituents for use herein include, but are not necessarily limited to, optionally branched $C_1$-$C_{20}$ alkoxy groups, (e.g. connected to the R1 and R2 groups through an oxygen bridging atom); optionally substituted $C_5$-$C_{14}$ aryloxy groups, (e.g. connected to the R1 and R2 groups through an oxygen bridging atom); optionally branched $C_1$-$C_{20}$ alkoxy($C_1$-$C_{20}$)alkyl groups, (e.g. a $C_1$-$C_{20}$ hydrocarbyl group bearing a $C_1$-$C_{20}$ alkoxy group); halides such as chloride, bromide and iodide; hydroxyl; amino; (di-)$C_1$-$C_6$ alkylamino; nitro; $C_1$-$C_6$ alkylsulphonyl; $C_1$-$C_6$ alkylthio($C_1$-$C_6$) alkyl groups; sulphate; heterocyclic groups, especially with at least one N and/or O ring atom; and tosyl groups.

Specific examples of suitable polar substituents include methoxy, ethoxy, isopropoxy, phenoxy, pentafluorophenoxy, trimethylsiloxy, dimethylamino, methylsulphonyl, tosyl, methoxymethyl, methylthiomethyl, 1,3-oxazolyl, hydroxyl, amino, methoxymethyl, phosphino, arsino, stibino, sulphate, nitro and the like.

Preferably, the polar substituents on the $R^1$ and $R^2$ groups are independently selected from optionally branched $C_1$-$C_{20}$ alkoxy groups, optionally substituted $C_5$-$C_{14}$ aryloxy groups, and optionally branched $C_1$-$C_{20}$ alkyl($C_1$-$C_{20}$)alkoxy groups. More preferably, the polar substituents are independently selected from optionally branched $C_1$-$C_{20}$ alkoxy groups, especially optionally branched $C_1$-$C_6$ alkoxy groups such as, for example, methoxy, ethoxy, propoxy, isopropoxy, butoxy, isobutoxy, tert-butoxy, pentoxy, isopentoxy, hexoxy or isohexoxy, of which methoxy, ethoxy and isopropoxy are particularly preferred polar substituent groups.

In one embodiment, the $R^1$ and/or $R^2$ groups independently bears a polar substituent on at least one of the ortho-positions. Said $R^1$ and/or $R^2$ group can also be optionally substituted by either a polar or non-polar group at any other position on the aromatic or heteroaromatic group.

For the avoidance of doubt, the phrase "bears a polar substituent on at least one of the ortho-positions" means, for example, that the $R^1$ and/or $R^2$ group is substituted with a polar substituent on one or both of its ortho positions.

By the term "ortho-position" when used in relation to substituents on the $R^1$ and $R^2$ groups, it is meant that the substituent is in the ortho position relative to the atom bonded to the phosphorus atom.

The $R^3$ group is selected from hydrogen, a hydrocarbyl group, a substituted hydrocarbyl group, a heterohydrocarbyl group, a substituted heterohydrocarbyl group, a silyl group or derivative thereof. Typically, $R^3$ is selected from hydrogen or the groups consisting of alkyl, substituted alkyl, aryl, substituted aryl, aryloxy, substituted aryloxy, alkenyl, substituted alkenyl, cycloalkyl, substituted cycloalkyl, alkoxycarbonyl, carbonyloxy, alkoxy, aminocarbonyl, carbonylamino, dialkylamino, silyl groups or derivatives thereof, and alkyl or aryl groups substituted with any of these substituents or halogen or a nitro group.

Preferably, the $R^3$ group is selected from a hydrocarbyl group, a substituted hydrocarbyl group, a heterohydrocarbyl group, a substituted heterohydrocarbyl group, a silyl group or derivative thereof. More preferably $R^3$ is an alkyl, substituted alkyl (including heterocyclic substituted alkyl with at least one heteroatom, such as N or O, and alkyl groups substituted with a heteroatom or heteroatomic group), cycloalkyl, substituted cycloalkyl, substituted cyclic aryl, substituted aryl, aryloxy or substituted aryloxy group.

Examples of suitable $R^3$ groups include $C_1$-$C_{15}$ alkyl groups, substituted $C_1$-$C_{15}$ alkyl groups, $C_1$-$C_{15}$ alkenyl groups, substituted $C_1$-$C_{15}$ alkenyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups and substituted $C_1$-$C_{15}$ alkoxy groups. Most preferred $R^3$ groups are the $C_1$-$C_{15}$ alkyl groups, which include both linear and branched alkyl groups; suitable examples include methyl, ethyl, propyl, isopropyl, butyl, isobutyl, tert-butyl, pentyl, alkyl branched pentyl groups, hexyl, alkyl branched hexyl groups, heptyl, alkyl branched heptyl groups, octyl and alkyl branched octyl groups.

Examples of suitable —N($R^3$)— groups include —N(methyl)-, —N(ethyl)-, —N(propyl)-, —N(isopropyl)-, —N(butyl)-, —N(t-butyl)-, —N(pentyl)-, —N(hexyl)-, —N(2-ethylhexyl)-, —N(cyclohexyl)-, —N(1-cyclohexylethyl)-, —N(2-methylcyclohexyl)-, —N(benzyl)-, —N(phenyl)-, —N(2-octyl)-, —N(4-methoxyphenyl)-, —N(4-tert-butylphenyl)-, —N(($CH_2$)$_3$—N-morpholine)-, —N(Si($CH_3$)$_3$)—, —N($CH_2CH_2CH_2$Si(OMe)$_3$))-, —N(decyl)- and —N(allyl)-.

In the compound of formula X—P($R^4$), the halide group, X, is typically selected from fluoride, chloride, bromide or iodide, preferably, fluoride, chloride or bromide, especially bromide or chloride.

The $R^4$ group is an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure.

Suitable examples of arylenedioxy groups include, but are not limited to, 1,2-phenylenedioxy, 1,2-dihydroxynaphthalene, 2,3-dihydroxynaphthalene, 1,2-dihydroxyanthracene, 1,2-dihydroxyphenanthrene, 2,3-dihydroxyphenanthrene, 3,4-dihydroxyphenanthrene, 9,10-dihydroxyphenanthrene, 1,8-dihydroxynaphthalene, 2,2'-dihydroxybiphenyl, and 2,2'-dihydroxy-1,1'-binaphthyl. The dimercapto and optionally substituted diamino analogues of these compounds are examples of suitable arylenedimercapto and arylenediamino groups, respectively.

Suitable alkylenedioxy groups include 2,3-dimethyl-2,3-butylenedioxy (=tetramethylethylenedioxy) and 1,3-propylenedioxy. The dimercapto and optionally substituted diamino analogues of these compounds are examples of suitable alkylenedimercapto and alkylenediamino groups, respectively.

In preferred embodiments, $R^4$ is an optionally substituted alkylenedioxy or arylenedioxy group. 1,2-alkylenedioxy or 1,2-arylenedioxy groups are most preferred, especially 1,2-arylenedioxy groups.

In a particularly preferred embodiment the $R^4$ group is an optionally substituted 1,2-arylenedioxy group having the following structure, which is bound to the phosphorus atom through the two ortho positioned oxygen atoms of the ortho-arylenedioxy structure, i.e.

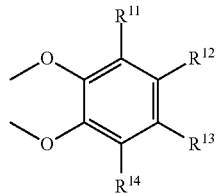

wherein the $R^{11}$ to $R^{14}$ groups on the phenyl ring are independently selected from hydrogen, hydrocarbyl groups, substituted hydrocarbyl groups, inert functional groups or any two of the $R^{11}$ to $R^{14}$ groups may be linked together to form a cyclic hydrocarbyl or heterohydrocarbyl structure.

Preferably, the $R^{11}$ to $R^{14}$ groups are independently selected from hydrogen, halogen, hydrocarbyl, heterohydrocarbyl, or two of the $R^{11}$ to $R^{14}$ groups are linked together to form a cyclic hydrocarbyl or heterohydrocarbyl structure.

Examples of suitable $R^{11}$ to $R^{14}$ groups include hydrogen, fluorine, chlorine, bromine, iodine, $C_1$-$C_{15}$ alkyl groups, substituted $C_1$-$C_{15}$ alkyl groups, $C_1$-$C_{15}$ alkenyl groups, substituted $C_1$-$C_{15}$ alkenyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups, substituted $C_1$-$C_{15}$ alkoxy groups, alcohol groups, amino groups and thiol groups. Alternatively, two of the $R^{11}$ to $R^{14}$ groups are linked together to form a cyclic hydrocarbyl or heterohydrocarbyl structure, examples of such structures include optionally substituted phenyl, biphenyl, naphthyl, binaphthyl, anthracenyl, phenanthryl, thiophenyl, pyridyl, cyclopentyl, cyclohexyl, ferrocenyl and tetrahydrofuranyl groups.

In one specific preferred embodiment, the $R^{11}$ to $R^{14}$ groups are hydrogen, i.e. ortho-phenylenedioxy.

In the ligand of formula (IV):

the $R^1$ group is selected from a hydrocarbyl, substituted hydrocarbyl, heterohydrocarbyl and substituted heterohydrocarbyl, as defined hereinabove; and
the $R^8$ group is selected from an aromatic or heteroaromatic group which comprises at least one polar substituent group, and optionally one or more non-polar substituent groups.

In the case of ligand (IV), it is preferable that the $R^1$ group is selected from an optionally substituted aromatic or optionally substituted heteroaromatic group, such as an optionally substituted phenyl, more preferably an optionally substituted aromatic or optionally substituted heteroaromatic group which comprises at least one polar substituent group, and optionally one or more non-polar substituent groups, such as a phenyl group substituted with at least one polar substituent.

In the case of ligand (IV), it is particularly preferred that $R^1$ and $R^8$ are both phenyl groups substituted with a polar group on at least one of the ortho positions.

In the case of ligand (VI):

$R^9$ and $R^{10}$ are independently selected from optionally substituted alkyl or heteroalkyl groups. Suitable alkyl groups include bulky alkyl groups have 4 or more carbon atoms, preferably alkyl groups having 4 to 8 carbon atoms. Suitable heteroalkyl groups include those bulky alkyl groups listed above wherein one or more of the carbon atoms is substituted with one or more heteroatoms such as Si, S, N or O. In preferred embodiments, $R^9$ and $R^{10}$ are both independently selected from an optionally substituted alkyl, preferably a C4-C8 alkyl, especially tert-butyl.

The ligands of general formulae (I) and (II) are prepared herein by a process which comprises reacting:
i) a compound having the general formula (III):

wherein $R^1$, $R^2$, $R^3$ are as defined above for formulae (I) and (II) and $R^5$ is selected from hydrogen and a $P(R^6)(R^7)$—group;
wherein $R^6$ and $R^7$ are independently selected from hydrocarbyl, substituted hydrocarbyl, heterohydrocarbyl and substituted heterohydrocarbyl groups; and
ii) a compound of the formula X—$P(R^4)$, wherein X is a halide and the $R^4$ groups is as defined above for ligands of general formulae (I) and (II); preferably at a temperature in the range of from −30 to 200° C.

Importantly, if the $R^5$ group is hydrogen, an HX acceptor compound must also be used. Suitable HX-acceptors for use herein include neopentyl lithium, n-butyl lithium, sec-butyl lithium, lithium hydride, sodium hydride, potassium hydride, triethylamine, trimethylamine, tripropylamine and the like.

In the case where $R^5$ is $P(R^6)(R^7)$, it should be noted that the ligand composition formed also comprises X—$P(R^6)(R^7)$ as by-product. This by-product does not interfere to any significant degree with an oligomerization reaction and therefore need not be removed from the resulting ligand composition prior to formation of a catalyst composition.

In preferred embodiments, $R^6$ and $R^7$ are selected from an aromatic or heteroaromatic group, preferably an aromatic group comprising at least one polar substituent group.

The product of the reaction of compound (III) with X—P($R^4$) may comprise a mixture of ligands in equilibrium with each other, for example, a mixture of ligands (I) and (II) with their P—N—P analogue $(R^1)(R^2)P$—$N(R^3)$—$P(R^4)$. Indeed, in the examples section below, the preparation of ligand F gives a 4:1 mixture of P—P=N and P—N—P structures. This mixture of ligands can be used as such in a catalyst composition, without first separating out the individual ligands. Hence according to another aspect of the present invention there is provided a ligand system comprising the product formed by reacting (i) a compound having the general formula (III) as defined hereinabove with a compound of formula X—$P(R^4)$ as defined hereinabove.

The ligand of general formula (IV) can be prepared by a process comprising reacting:
(i) a compound having the general formula (V)

$$(R^1)(R^8)P—N(R^3)—R^5 \quad (V)$$

wherein $R^1$, $R^8$, $R^3$ and $R^5$ are as defined hereinabove; and
(ii) a compound of formula X—P($R^4$) wherein X and $R^4$ are defined hereinabove;
and if the R5 group is H, an HX-acceptor, preferably at a temperature of from −30° C. to 200° C.

The ligand of formula (VI) can be prepared by a process comprising reacting:
(i) a compound having the general formula (VII)

$$(R^9)(R^{10})P—N(R^3)—R^5 \quad (VII)$$

wherein $R^9$, $R^{10}$, $R^3$ and $R^5$ are as defined hereinabove; and
(ii) a compound of formula X—P($R^4$) wherein X and $R^4$ are defined hereinabove,
and if the R5 group is H, an HX-acceptor, preferably at a temperature of from −30° C. to 200° C.

The ligands and ligand systems of the present invention are useful in catalyst compositions for the oligomerization of olefins. The catalyst compositions of the present invention comprise:
(a) a source of chromium, molybdenum or tungsten;
(b) one or more ligands or ligand systems as described herein; and
(c) a cocatalyst.

The source of chromium, molybdenum or tungsten, component (a), for the catalyst system of the present invention can include simple inorganic and organic salts of chromium, molybdenum or tungsten. Examples of simple inorganic and organic salts are halides, acetylacetonates, carboxylates, oxides, nitrates, sulfates and the like. Further sources of chromium, molybdenum or tungsten can also include co-ordination and organometallic complexes, for example chromium trichloride tris-tetrahydrofuran complex, (benzene)tricarbonylchromium, chromium hexacarbonyl, and the like. Preferably, the source of chromium, molybdenum or tungsten, component (a), for the catalyst system is selected from simple inorganic and organic salts of chromium, molybdenum or tungsten.

In one embodiment of the present invention, the source of chromium, molybdenum or tungsten, component (a), for the catalyst system is a simple inorganic or organic salt of chromium, molybdenum or tungsten, which is soluble in a solvent such as those disclosed in U.S. Pat. No. 7,141,633 which is herein incorporated by reference.

The source of chromium, molybdenum or tungsten can also include a mixture of any combination of simple inorganic salts, simple organic salts, co-ordination complexes and organometallic complexes.

In a preferred embodiment herein, component (a) is a source of chromium, particularly chromium (III).

Preferred sources of chromium for use herein are simple inorganic and organic salts of chromium and co-ordination or organometallic complexes of chromium. More preferred sources of chromium for use herein are the simple inorganic and organic salts of chromium, such as salts of carboxylic acids, preferably salts of alkanoic acids containing 1 to 30 carbon atoms, salts of aliphatic-β-diketones and salts of β-ketoesters (e.g. chromium (III) 2-ethylhexanoate, chromium (III) octanoate and chromium (III) acetylacetonate), and halide salts of chromium, such as chromium trichloride, chromium trichloride tris-tetrahydrofuran complex, chromium tribromide, chromium trifluoride, and chromium tri-iodide. Specific examples of the preferred source of chromium for use herein is chromium (III) acetylacetonate, also called chromium tris(2,4-pentanedionate), Cr(acac)$_3$, chromium trichloride, CrCl$_3$, and chromium trichloride tris-tetrahydrofuran complex, CrCl$_3$(THF)$_3$.

The cocatalyst, may in principle be any compound or mixture of compounds that generates an active catalyst system with the source of chromium, molybdenum or tungsten, component (a), and the ligand, component (b).

Compounds which are suitable for use as a cocatalyst include organoaluminium compounds, organoboron compounds, organic salts, such as methyllithium and methylmagnesium bromide and the like.

Particularly preferred cocatalysts are organoaluminium compounds. Suitable organoaluminium compounds for use herein are those having the formula AlR$^{15}_3$, wherein each R$^{15}$ group is independently selected from C$_1$-C$_{30}$ alkyl (preferably C$_1$-C$_{12}$ alkyl), oxygen containing moieties and halides, and compounds such as LiAlH$_4$ and the like. Non-limiting examples of suitable organoaluminium compounds include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride and aluminoxanes (also called aluminoxanes). Mixtures of organoaluminium compounds are also suitable for use herein.

In a preferred embodiment herein, the cocatalyst is an aluminoxane cocatalyst. These aluminoxane cocatalysts may comprise any aluminoxane compound or a mixture of aluminoxane compounds. Aluminoxanes may be prepared by the controlled addition of water to an alkylaluminium compound, such as those mentioned above, or are available commercially. In this context it should be noted that the term "aluminoxane" as used within this specification includes commercially available aluminoxanes, which are derived from the corresponding trialkylaluminium by addition of water and which may contain from 2 to 15% wt., typically about 5% wt., but optionally about 10% wt., of aluminium.

Other suitable co-catalysts include those disclosed in U.S. Pat. No. 7,141,633, U.S. Published Patent Applications Nos. 2006/0128910, 2006/0173226, 2006/0211903, and 2006/0229480, which are incorporated herein in their entirety by reference.

The components of the catalyst system may be added together simultaneously or sequentially in any order so as to provide an active catalyst. The three catalyst components of the catalyst system, (a), (b) and (c), may be contacted in the presence of any suitable solvent. Suitable solvents are known to those skilled in the art, suitable solvents may include any inert solvent that does not react with the co-catalyst component, such as saturated aliphatic, unsaturated aliphatic, aromatic, halogenated hydrocarbons and ionic liquids. Typical solvents include, but are not limited to, benzene, toluene, xylene, ethylbenzene, cumene, propane, butane, pentane, heptane, decane, dodecane, tetradecane, methylcyclohexane, methylcyopentane, cyclohexane, 1-hexene, 1-octene and the like. Other examples of suitable solvents are those disclosed in U.S. Pat. No. 7,141,633, such as hydrocarbon solvents and polar solvents such as diethyl ether, tetrahydrofuran, dichloromethane, chloroform, chlorobenzene and the like.

The ligand, component (b), can either be formed prior to the formation of the catalyst, can be formed simultaneously with the formation of the catalyst or a catalyst precursor comprising catalyst components (a) and (b), or can be formed in-situ under an olefinic monomer, e.g. an ethylene, atmosphere. If the ligand is formed prior to the formation of the catalyst, this is typically performed by reacting the compound having the general formula (III), (V) or (VII) and the compound of the formula X—P(R$^4$) in a solvent, such as those mentioned above, at a temperature in the range of from −30 to 200° C. Depending on R$^5$=H or R$^5$=P(R$^6$)(R$^7$) temperature is either below 0 and 100° C., respectively. The reaction of the compound having the general formula (III), (V) or (VII) and the compound of the formula X—P(R$^4$) can be performed under an inert atmosphere.

Because the by-product formed in the reaction of the compound having the general formula (III), (V) and (VII) and the compound of the formula X—P(R$^4$) does not interfere with the catalytic activity of the catalyst composition, it is not necessary to isolate the ligand having the formula (I), (II), (IV) and/or (VI). Since the catalytic activity of the catalyst composition is independent of the presence of the by-product compound, the optional isolation of the ligand having the formula (I), (II), (IV) or (VI) by any method known in the art, and using said isolated ligand in the catalyst composition are also included herein. It is, however, observed that the absence of co-produced (R$^6$)(R$^7$)P—X e.g. (o-anisyl)$_2$P—Cl, as in the case of the isolated ligands, leads to higher activity of the catalyst system as evidenced by the higher Turnover Frequencies (TOF's). The methods of preparation described hereinabove in which the R$^5$ group in the compounds of formula (III), (V) or (VII) is hydrogen, advantageously does not produce (R$^6$)(R$^7$)P—X as by-product.

In one embodiment of the present invention, the catalyst system is formed by adding the co-catalyst component, (c), to a catalyst precursor composition comprising components (a) and (b).

The catalyst system of the present invention may be prepared either in the presence (i.e. "in-situ") or absence of the olefinic monomer. The three catalyst components of the catalyst system, (a), (b) and (c), may be combined fully in the absence of the olefinic monomer, or the olefinic monomer may be included prior to contacting the components of the catalyst system, simultaneously with the components of the catalyst system or at any point in the process of contacting the components of the catalyst.

The three components of the catalyst system, (a), (b) and (c), if component (b) has been preformed, may be combined at a temperature in the range of from −100 to 200° C., preferably 0 to 150° C., more preferably 20 to 100° C., and, if (b) has not been preformed, may be combined at a temperature in the range of from 30 to 200° C., preferably 50 to 150° C., more preferably 70 to 150° C.

The catalyst system of the process of the present invention may be unsupported or supported on a support material. Examples of suitable support materials can be found in U.S. Pat. No. 7,141,633 and U.S. Published Patent Applications Nos. 2006/0128910, 2006/0173226, 2006/0211903, and 2006/0229480, which are incorporated herein in their entirety by reference.

The quantity of cocatalyst in the catalyst system the present invention is typically enough to provide a ratio in the range from 0.1 to 20,000, preferably from 1 to 2000, more preferably 1 to 1000, most preferably 1 to 500, aluminium or boron atoms per atom of chromium, molybdenum or tungsten.

The amount of chromium, molybdenum or tungsten, and the amount of the ligand, can be present in the catalyst composition in a molar ratio in the range from 10000:1 to 1:10000, preferably from 100:1 to 1:100, more preferably from 10:1 to 1:10. Most preferably, the chromium, molybdenum or tungsten, and the ligand are present in a molar ratio in the range from 3:1 to 1:3. Generally the amount of chromium, molybdenum or tungsten, and the amount of ligand are approximately equal or double, i.e. a molar ratio in the range from 1.5:1 to 1:3.

The olefinic monomers suitable for use in the trimerization and tetramerization process of the present invention can be any olefinic monomers, which can be converted into a trimer or tetramer. Suitable olefinic monomers include, but are not necessarily limited to, ethylene, propylene, optionally branched $C_4$-$C_{24}$, preferably $C_4$-$C_{20}$ α-olefins, optionally branched $C_4$-$C_{24}$, preferably $C_4$-$C_{20}$ internal olefins, optionally branched $C_4$-$C_{24}$, preferably $C_4$-$C_{20}$ vinylidene olefins, optionally branched $C_4$-$C_{24}$, preferably $C_4$-$C_{20}$ cyclic olefins and optionally branched $C_4$-$C_{24}$, preferably $C_4$-$C_{20}$ dienes, as well as optionally branched $C_4$-$C_{24}$, preferably $C_4$-$C_{20}$ functionalized olefins. Examples of suitable olefinic monomers include, but are not necessarily limited to, linear α-olefins, such as ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene and 1-eicosene; branched α-olefins such as 4-methylpent-1-ene and 1-ethyl-1-hexene; linear and branched internal-olefins such as 2-butene; styrene; cyclohexene; norbornene and the like.

Mixtures of olefinic monomers can also be used in the process of the present invention.

Preferred olefinic monomers for use in the trimerization and tetramerization process of the present invention are propylene and ethylene. Especially preferred is ethylene.

The catalyst system and process of the present invention are particularly useful for the oligomerization of ethylene with a high selectivity towards 1-hexene and 1-octene.

The oligomerization reaction can be performed in solution phase, slurry phase, gas phase or bulk phase.

When the oligomerization is performed in solution or slurry phase, a diluent or solvent, which is substantially inert under the oligomerization conditions may be employed. Suitable diluents or solvents are aliphatic and aromatic hydrocarbons, halogenated hydrocarbons and olefins which are substantially inert under oligomerization conditions may be employed, such as those disclosed in U.S. Pat. No. 7,141,633 and U.S. Published Patent Applications Nos. 2006/0128910, 2006/0173226, 2006/0211903, and 2006/0229480, which are incorporated herein in their entirety by reference.

The oligomerization process of the present invention may be performed in any one of a number of suitable reactors, which are well known to one skilled in the art. Typically the oligomerization process of the present invention is carried out in a batch, semi-batch or continuous mode.

The oligomerization process of the present invention may be carried out under the following range of reaction conditions. Typically, the temperature will be in the range from about 0° C. to about 150° C., preferably from about 30° C. to about 150° C., and more preferably from about 70° C. to about 150° C. The pressure range under which the process of the present invention may be performed is typically in the range of from below atmospheric pressure to about 100 barg. Preferably, the pressure will be in the range from about 0.1 to about 80 barg, more preferably from about 0.5 to about 70 barg, especially in the range of from about 1 to about 60 barg. Temperatures and pressures outside those stated above may also be employed, however, the reaction product slate will either have an excess of heavy and/or solid by-products or an insignificant amount of the trimer or tetramer.

By varying the temperature and pressure it is possible for ratio of trimers and tetramers produced in the process of the present invention to be varied. A trend observed indicates that the amount of trimers produced in the process of the present invention increases with increasing temperature. Another trend which has been observed indicates that the amount of tetramers produced in the process of the present invention increases with increasing pressure.

Therefore, by varying the reaction conditions of the process of the present invention, the amount of trimers and tetramers in the oligomerization product composition may be varied. This may be useful for a continuous or semi-continuous oligomerization process which produces a high proportion of trimers and tetramers, wherein the product composition can be changed (e.g. from producing a higher proportion of trimers to a higher proportion of tetramers, or vice-versa,) by changing the reactor conditions without having to interrupt the olefinic monomer feed or the oligomerization product flow. In particular, this may be especially useful for a continuous or semi-continuous process for the oligomerization of ethylene, wherein the product composition can be changed (e.g. from producing a higher proportion of 1-hexene to a higher proportion of 1-octene, or vice-versa) by changing the reactor conditions without having to interrupt the olefinic monomer feed or the oligomerization product flow.

In one embodiment of the present invention, there is a process for the oligomerization of olefinic monomers, wherein the process comprises contacting at least one olefinic monomer under oligomerization reaction conditions with a catalyst system of the process of the present invention, wherein the process is a continuous or semi-continuous process and the reaction conditions are varied during the process. Variation of the reaction conditions can be performed to make continual adjustments to a process to ensure a consistent product composition or can be performed to a process to change the product composition produced. A preferred version of this embodiment is a process for the oligomerization of ethylene, wherein the process comprises contacting ethylene with a catalyst system of the process of the present invention, wherein the process is a continuous or semi-continuous process and the reaction conditions are varied during the process.

Separation of the products, reactant and catalyst can be performed by any technique known to one skilled in the art, such as distillation, filtration, centrifugation, liquid/liquid separation, extraction, and the like.

Further details regarding reactors, solvents, separation techniques, and the like, can be found in U.S. Pat. No. 7,141,633 which is herein incorporated by reference.

The use of the process of the present invention for the catalytic oligomerization of olefinic monomers provides a simple method for producing trimers and tetramers of the olefinic monomer. In particular, the use of the process of the present invention for the catalytic oligomerization of ethylene provides a simplified method for producing 1-hexene and 1-octene, with very high selectivity for 1-hexene and 1-octene over all the other products formed in the $C_6$ and $C_8$ fractions respectively.

The overall yield of 1-hexene and 1-octene in the process for the trimerization and tetramerization of ethylene of the present invention depends upon the reaction conditions employed.

Typically, the trimerization and tetramerization selectivity (i.e. the amount of trimers and tetramers of the olefinic monomers in the overall product composition) of the process of the present invention is at least 60% wt, preferably at least 70% wt, more preferably at least 80% wt, of the overall product composition. The trimerization and tetramerization selectivity for the trimerization and tetramerization of ethylene (i.e. the amount of $C_6$ and $C_8$ fraction in the overall product composition) using the process of the present invention is at least 60% wt, preferably at least 70% wt, more preferably at least 80% wt, of the overall product composition.

The amount of 1-hexene produced by the trimerization and tetramerization of ethylene using the process of the present invention is typically in the range of from 10% wt to 90% wt, preferably from 11% wt to 85% wt, more preferably from 12% wt to 80% wt, of the overall product composition. The amount of 1-octene produced by the trimerization and tetramerization of ethylene using the process of the present invention is typically in the range of from 10% wt to 90% wt, preferably from 11% wt to 85% wt, more preferably from 12% wt to 80% wt, of the overall product composition.

The 1-hexene selectivity (i.e. the amount of 1-hexene present in the $C_6$ fraction of the product composition) in the trimerization and tetramerization of ethylene using the process of the present invention is preferably at least 85% wt, more preferably at least 90% wt, most preferably at least 92% wt of the $C_6$ fraction of the product composition.

The 1-octene selectivity (i.e. the amount of 1-octene present in the $C_8$ fraction of the product composition) in the trimerization and tetramerization of ethylene using the process of the present invention is preferably at least 85% wt, more preferably at least 90% wt, most preferably at least 92% wt, of the $C_8$ fraction product composition.

The amount of $C_{10}$ produced in the trimerization and tetramerization of ethylene using the process of the present invention is typically at most about 10% wt.

The amount of solids produced in the trimerization and tetramerization of ethylene using the process of the present invention is typically at most about 5% wt. Lower levels of solid olefin waxes and polyethylene produced in the trimerization and tetramerization of ethylene are desirable in commercial operations as this can reduce the amount of fouling of the reactor equipment, reduce the amount of waste by-products and reduce the amount of operational "downtime" due to maintenance and cleaning of the reactor equipment.

In one embodiment of the present invention, the olefinic product composition of the oligomerization of ethylene using the process of the present invention typically comprises a combined total content of 1-hexene and 1-octene in the range of from 60 to 98% wt of the overall product composition, preferably from 70 to 98% wt and more preferably from 80 to 100% wt, wherein the 1-hexene content is typically at least 10% wt of the overall product composition, the 1-hexene selectivity is typically at least 90% wt of the $C_6$ fraction of the product composition, the 1-octene content is typically at least 10% wt of the overall product composition, the 1-octene selectivity is typically at least 90% wt of the $C_8$ fraction of the product composition, and the amount of solids produced is at most about 5% wt of the overall product composition.

In another embodiment of the present invention, the olefinic product composition of the trimerization and tetramerization of ethylene using the process of the present invention comprises a total content of compounds other than 1-hexene and 1-octene of at most 40% wt of the overall product composition, preferably at most 30% wt and more preferably at most 20% wt, wherein the 1-hexene content is typically at least 10% wt of the overall product composition, the 1-hexene selectivity is typically at least 90% wt of the $C_6$ fraction of the product composition, the 1-octene content is typically at least 10% wt of the overall product composition, the 1-octene selectivity is typically at least 90% wt of the $C_8$ fraction of the product composition, and the amount of solids produced is at most about 5% wt of the overall product composition.

The process of the present invention is illustrated by the following non-limiting examples.

EXAMPLES

General Procedures and Characterisation

All chemicals used in preparations were purchased from Aldrich and used without further purification unless mentioned otherwise.

All the operations with the catalyst systems were carried out under nitrogen atmosphere. All solvents used were dried using standard procedures. Anhydrous toluene (99.8% purity) was dried over 4 Å molecular sieves (final water content of about 3 ppm).

Ethylene (99.5% purity) was purified over a column containing 4 Å molecular sieves and BTS catalyst (BASF) in order to reduce water and oxygen content to <1 ppm.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 µm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene. The yields of the $C_4$-$C_{30}$ olefins were obtained from the GC analysis.

The amount of "solids", mainly consisting of heavy wax and polyethylene, has been determined by weighing, after its isolation from the reactor wall and appendages, followed by washing with toluene on a glass filter (P3) and by vacuum drying.

The amount of "total product" is the sum of the amount of largely olefinic product derived from GC analysis and the amount of solids.

The NMR data was obtained at room temperature with a Varian 300 MHz or 400 MHz apparatus.

Catalyst Compositions

A number of catalyst systems containing ligand compositions A, A', B', C''', C', C*, D''', D', E, F, G''', H''', K''', L, M''', N''', Q, T', U and V and a chromium source were prepared and used in the oligomerisation reactions described below.

Chromium Source

Chromium tris-(2,4-pentanedionate), also called chromium tris(acetylacetonate), was used as the chromium source throughout.

Ligand Composition A

The reaction product of (2-methoxyphenyl)$_2$PNH(methyl) and (o-phenylenedioxy)PCl (ligand composition A) was prepared as follows.

Under a nitrogen atmosphere 1.015 g (3.62 mmol) (2-methoxyphenyl)$_2$PCl (available from Aldrich) was added to 10 ml methylamine (2M in THF) in 50 ml pentane. The resulting mixture was stirred overnight at room temperature. The precipitate was removed by centrifugation. The solvents were removed from the resulting solution under vacuum. Washing with pentane yielded 0.85 g (3.09 mmol; (84%)) (2-methoxyphenyl)$_2$PNH(methyl) as a white solid. $^{31}$P-NMR (in $C_6D_6$) δ 31.6.

Under a nitrogen atmosphere, 133 mg (1.70 mmol) of neopentyl lithium was slowly added to 428 mg (1.55 mmol) of (2-methoxyphenyl)$_2$PNH(methyl) in 60 ml dry toluene. To the resulting mixture 280 mg (1.60 mmol) (o-phenylenedioxy)PCl (available from Aldrich) in 5 ml toluene was slowly added. The mixture was stirred for 2 hours at room temperature. To the mixture 25 ml pentane was added. The precipitate was removed by centrifugation. The solvent was removed under vacuum. The resulting sticky material was washed with pentane (twice) and a white solid was isolated. According to $^{31}$P-NMR the product consisted at least predominantly of a P—P=N(methyl) structure with on one P atom the o-phenylenedioxy group and on the other P atom two 2-methoxyphenyl groups (either (o-phenylenedioxy)P (2-methoxyphenyl)$_2$PN(methyl) or (2-methoxyphenyl)$_2$P(o-phenylenedioxy)PN(methyl)). $^{31}$P-NMR (in $C_6D_6$) signals at δ 153.1 and 35.3 ($J_{PP}$=359 Hz).

Ligand Composition A'

The reaction product of (2-methoxyphenyl)$_2$PN(methyl)P (2-methoxyphenyl)$_2$ and (o-phenylenedioxy)PCl (ligand composition A') was prepared as follows.

Under a nitrogen atmosphere, 87 mg (o-phenylenedioxy) PCl (available from Aldrich) was added to 260 mg (2-methoxyphenyl)$_2$PN(methyl)P(2-methoxyphenyl)$_2$ (Ligand composition K''') in 2 ml dry toluene. The resulting mixture was heated to 110° C. overnight.

The solvent was removed from the solution by heating under vacuum. Part of the resulting mixture was dissolved in pentane, the pentane solution was isolated and subsequently the solvent was removed and the residue was dried under vacuum. According to $^{31}$P-NMR spectroscopy, the product was an approximately 1 to 1 (mol/mol) mixture of (2-methoxyphenyl)$_2$PCl and a P—P=N(methyl) structure with on one P atom the o-phenylenedioxy group and on the other P atom two 2-methoxyphenyl groups (either (o-phenylenedioxy)P(2-methoxyphenyl)$_2$PN(methyl) or (2-methoxyphenyl)$_2$P(o-phenylenedioxy)PN(methyl)). $^{31}$P-NMR (in $C_6D_6$) δ 153.1 and 35.3 ($J_{PP}$=359 Hz).

This mixture was used as such in the catalyst for ethylene oligomerization experiments without further purification.

Ligand Composition B'

The reaction product of (2-methoxyphenyl)(phenyl)PN (methyl)P(phenyl)(2-methoxyphenyl) and (o-phenylenedioxy)PCl (ligand composition B') was prepared as follows.

The (2-methoxyphenyl)(phenyl)PN($CH_3$)P(2-methoxyphenyl)(phenyl) ligand was prepared by first forming a suspension of 0.42 g lithium (60 mmol) in 80 ml of tetrahydrofuran (THF), to which was added 9.66 g of (2-methoxyphenyl)$_2$P(phenyl) (30 mmol) at 0° C. under an argon atmosphere. The mixture was stirred for 4 hours, after which time a 5 ml aliquot of methanol was added. 60 ml of toluene was added to the mixture, after which the solution was extracted with two 40 ml portions of water. The extracted toluene solution was then concentrated to a volume of approximately 20 ml, which resulted in formation of a suspension. The concentrated toluene solution was filtered, and 4.6 g of $C_2Cl_6$ was added to the toluene filtrate, which was then stirred for 2 hours at 90° C. The HCl gas, which evolved from the reaction, was "trapped" in an alkali bath. The mixture was then cooled to room temperature and purged with nitrogen to remove all of the remaining HCl present in the solution.

At room temperature, a 5 ml aliquot of triethylamine was added to the concentrated toluene solution and left for a few minutes, after which 6 ml of 2 M $H_2NMe$ (12 mmol) was added a few drops at a time. The suspension was filtered and washed with 20 ml of toluene. The toluene filtrate and the toluene wash fraction were combined. The combined toluene fractions were evaporated to dryness and 30 ml of methanol was added. The methanol solution was left overnight at −35° C. wherein a white (2-methoxyphenyl)(phenyl)PN($CH_3$)P(2- methoxyphenyl)(phenyl) precipitate was formed in the solution. The precipitated ligand was then isolated.

The precipitated ligand consisted of two isomers, a racemic isomer (the RR and/or the SS enantiomers of the ligand) and a meso isomer (the RS enantiomer of the ligand). The proportions of these two isomers were determined by $^{31}$P NMR with peaks at 63.18 and 64.8 ppm corresponding to the two different isomers respectively. These two samples consisted of mixtures of both the racemic and the meso isomers having weight ratios of 57/43 and 92/8 respectively. Only the sample of (2-methoxyphenyl)(phenyl)PN(CH$_3$)P(2-methoxyphenyl)(phenyl) with the racemic and the meso isomers in a weight ratio of 57/43 was used.

Under a nitrogen atmosphere, 14 mg (o-phenylenedioxy)PCl was added to 37 mg (2-methoxyphenyl)(phenyl)PN(methyl)P(phenyl)(2-methoxyphenyl) in 1.0 ml dry C$^6$D$_6$. The resulting mixture was heated overnight in an oil bath at 90° C.

Based on the $^{31}$P-NMR spectrum, the main products were an approximate 1 to 1 (mol/mol) mixture of (2-methoxyphenyl)(phenyl)PCl and a P—P=N(methyl) structure with on one P atom the o-phenylenedioxy group and on the other P atom one 2-methoxyphenyl group and one phenyl group (either (o-phenylenedioxy)P(2-methoxyphenyl)(phenyl)PN(methyl) or (2-methoxyphenyl)(phenyl)P(o-phenylenedioxy)PN(methyl)). $^{31}$P-NMR (in C$_6$D$_6$) δ 151.7 and 43.0 ($J_{PP}$=353 Hz).

This mixture was used as such in the catalyst for ethylene oligomerization experiments without further purification.

Ligand Composition C'', Ligand Composition C' and Ligand Composition C*

The reaction product of (2-methoxyphenyl)$_2$PNH(isopropyl) and (o-phenylenedioxy)PCl (ligand composition C'') was prepared as follows.

Under a nitrogen atmosphere, 3 ml triethylamine was added to 1.5 ml isopropylamine (17.6 mmol) in 5 ml dry toluene. To the resulting mixture, 2.2 g (7.84 mmol) (2-methoxyphenyl)$_2$PCl in 20 ml toluene was slowly added and allowed to stir overnight at room temperature. The precipitate was removed by centrifugation. The solvents were removed from the resulting solution in vacuo. Washing with pentane yielded (2-methoxyphenyl)$_2$PNH(isopropyl) as a white solid. $^{31}$P-NMR in C$_6$D$_6$) δ 21.8.

Under a nitrogen atmosphere, 60 mg (0.77 mmol) of neopentyl lithium was slowly added to 226 mg of (2-methoxyphenyl)$_2$PNH(isopropyl) in 20 ml dry toluene. To the resulting mixture 130 mg (0.75 mmol) (o-phenylenedioxy)PCl in 1 ml toluene was slowly added. The mixture was stirred for 2 hours at room temperature. The precipitate was removed by centrifugation. The solvent was removed in vacuo. After washing with methanol a product, which according to $^{31}$P-NMR had at least predominantly the P—N(isopropyl)-P structure, i.e. (2-methoxyphenyl)$_2$PN(isopropyl)P(o-phenylenedioxy), was isolated as a white solid. $^{31}$P-NMR (in C$_6$D$_6$) δ 156.9 and 11.6 ($J_{PP}$=~20 Hz).

According to $^{31}$P-NMR spectroscopy the same P—N—P product as present in ligand composition C'', (2-methoxyphenyl)$_2$PN(isopropyl)P(o-phenylenedioxy), was formed almost quantitatively upon reaction of (o-phenylenedioxy)PCl with ligand composition N'', (2-methoxyphenyl)$_2$PN(isopropyl)P(Phenyl)$_2$ overnight in C$_6$D$_6$ at 80° C. with concomitant formation of an equivalent amount of (phenyl)$_2$PCl (designated ligand composition C'). $^{31}$P-NMR (in C$_6$D$_6$) δ 157 and 12.

According to $^{31}$P-NMR spectroscopy the same P—N—P product as present in ligand composition C'', (2-methoxyphenyl)$_2$PN(isopropyl)P(o-phenylenedioxy), was formed almost quantitatively upon reaction of (o-phenylenedioxy)PCl with P—P=N ligand composition L, (2-methoxyphenyl)$_2$P—P (2-methoxyphenyl)$_2$=N(isopropyl) during <0.5 hour in C$_6$D$_6$ at 20° C. with concomitant formation of an equivalent amount of (2-methoxyphenyl)$_2$P—Cl (designated ligand composition C*). $^{31}$P-NMR (in C$_6$D$_6$) δ 157 and 12.

Ligand Composition D'' and Ligand Composition D'(Comparative)

The (phenyl)$_2$PN(isopropyl)P(o-phenylenedioxy) ligand composition was prepared according to the method reported in Heteroatom Chem. Vol. 2, 477 (1991).

Under a nitrogen atmosphere, 12 ml triethylamine was added to 3.39 g isopropylamine in 10 ml dry toluene. To the resulting mixture, 5.15 ml (phenyl)$_2$PCl (available from Aldrich) was slowly added and allowed to stir overnight at room temperature. The precipitate was removed by filtration. The solvents were removed from the resulting solution in vacuo. To the evaporation residue, pentane was added. The solvent was then removed in vacuo from the pentane solution, yielding (phenyl)$_2$PNH(isopropyl) as a colourless oil, which crystallized on standing at room temperature. $^{31}$P-NMR (in C$_6$D$_6$) δ 35.8.

Under a nitrogen atmosphere, 1.7 ml triethyl amine was added to 2.00 g of (phenyl)$_2$PNH(isopropyl) in 10 ml dry toluene. The resulting mixture was cooled to approximately 0° C. and 1.435 g of (o-phenylenedioxy)PCl (available from Aldrich) was slowly added. The mixture was then stirred overnight at room temperature (approximately 20° C.).

The precipitate which formed in the solution was removed by centrifugation. The resulting solution was concentrated under vacuum and was subsequently filtered over silica gel.

The solvent was removed under vacuum, which yielded a white solid of (phenyl)$_2$PN(isopropyl)P(o-phenylenedioxy). $^{31}$P-NMR (in C$_6$D$_6$) δ 157.4 and 30.0 ($J_{PP}$=17 Hz).

According to $^{31}$P-NMR spectroscopy the same P—N—P product as present in ligand composition D'', (phenyl)$_2$PN(isopropyl)P(o-phenylenedioxy), was formed in about 10% yield upon reaction of (o-phenylenedioxy)PCl with ligand composition M'', (phenyl)$_2$PN(isopropyl)P(phenyl)$_2$ overnight in C$_6$D$_6$ at 90° C. with concomitant formation of (phenyl)$_2$PCl (designated ligand composition D'). The remainder of the reaction mixture were predominantly starting components. $^{31}$P-NMR (in C$_6$D$_6$) δ 157 and 30.

Ligand Composition E

The reaction product of (phenyl)$_2$PNH(methyl) and (o-phenylenedioxy)PCl (ligand composition E) was prepared as follows.

Under a nitrogen atmosphere, 400 mg triethylamine was added to 2 ml methylamine (2 M in THF) in 5 ml dry toluene. The resulting solution was cooled to −15° C. and 440 mg (phenyl)$_2$PCl in 5 ml toluene was slowly added and allowed to stir overnight at room temperature. To the resulting mixture pentane was added. The precipitate was removed by centrifugation. The solvents were removed under vacuum. The resulting sticky product was extracted with cold pentane. After removing the pentane under vacuum (phenyl)$_2$PNH(methyl) was isolated as an oil. $^{31}$P-NMR (in C$_6$D$_6$) δ 45.7.

To 55 mg (phenyl)$_2$PNH(methyl) in 1 ml C$_6$D$_6$ was added 50 mg triethylamine and 44 mg (o-phenylenedioxy)PCl. After standing overnight 2 ml of pentane was added. The precipitate was removed by centrifugation. The solvents were removed under vacuum. The product was isolated as an oil. According to $^{31}$P-NMR the product consisted at least predominantly of a P—P=N(methyl) structure with on one P atom the o-phenylenedioxy group and on the other P atom two phenyl groups (either (O-phenylenedioxy)P(phenyl)$_2$PN(methyl) or (phenyl)$_2$P(o-phenylenedioxy)PN(methyl)). $^{31}$P-NMR (in C$_6$D$_6$) δ 151.9 and 49.1 ($J_{PP}$=351 Hz).

Ligand Composition F

The reaction product of (tert-butyl)$_2$PNH(methyl) and (o-phenylenedioxy)PCl (ligand composition F) was prepared as follows.

Under a nitrogen atmosphere, 3 ml triethylamine was added to 6 ml methylamine (2 M in THF) in 20 ml dry toluene. To the resulting solution, 1.6 g (tert-butyl)$_2$PCl (available from Aldrich) was slowly added and allowed to stir overnight at room temperature. To the resulting mixture pentane was added. The precipitate was removed by centrifugation. The solvents were removed under vacuum. The resulting oil was crystallized from pentane (−20° C.). Yielding white crystals of (tert-butyl)$_2$PNH(methyl). $^{31}$P-NMR (in C$_6$D$_6$) δ 82.8. This product has been described as an oil in Phosphorus, Sulfur and Silicon, 1990, vol. 54, p. 55-61.

Under a nitrogen atmosphere, 95 mg triethylamine was added to 83 mg (tert-butyl)$_2$PNH(methyl) in 3 ml dry toluene. To the resulting solution, 83 mg (o-phenylenedioxy)PCl was slowly added and allowed to stir overnight at room temperature. To the resulting mixture pentane was added. The precipitate was removed by centrifugation. The solvents were removed under vacuum. The resulting white solid was washed with cold pentane. The $^{31}$P-NMR spectrum in C$_6$D$_6$ showed 2 products one with a set of doublets at δ 151.2 and 84.7 (J$_{PP}$=375) and one with a set of doublets at δ 153.8 and 115.8 (J$_{PP}$=42 Hz) in a 4 to 1 (mol/mol) ratio. Most probably the product consisted of a 4 to 1 (mol/mol) mixture of isomers having a P—P=N(methyl) structure with on one P atom the o-phenylenedioxy group and on the other P atom two tert-butyl groups (either (o-phenylenedioxy)P(tert-butyl)$_2$PN (methyl) or (tert-butyl)$_2$P(o-phenylenedioxy)PN(methyl)) and a P—N(methyl)-P structure, (tert-butyl)$_2$P—N(methyl)-P(o-phenylenedioxy).

Ligand Composition G"

The reaction product of (2-methoxyphenyl)$_2$PNH(pentafluorophenyl) and (o-phenylenedioxy)PCl (ligand composition G") was prepared as follows.

Under a nitrogen atmosphere, 0.5 g (6.3 mmol) of neopentyllithium (available from Aldrich) was slowly added to 1.15 g (6.3 mmol) pentafluoroaniline (available from Aldrich) in 25 ml dry toluene and stirred for 0.5 hour at room temperature. To the resulting mixture 1.76 g (6.3 mmol) (2-methoxyphenyl)$_2$PCl in 15 ml toluene was slowly added and allowed to stir for 1 hour at room temperature. The precipitate was removed by centrifugation. The solution was concentrated to about 5 ml. Pentane was added (about 20 ml), the precipitate was collected. Washing with pentane yielded (2-methoxyphenyl)$_2$PNH(C$_6$F$_5$) as a white solid. $^{31}$P-NMR (in C$_6$D$_6$) δ 38.4 (t) (J$_{PF}$=60 Hz). $^{19}$F-NMR (in C$_6$D$_6$) δ −156 (o); −165.2 (m); −170.3 (p).

Under a nitrogen atmosphere, 128 mg (1.64 mmol) of neopentyllithium was slowly added to 700 mg (1.64 mmol) (2-methoxyphenyl)$_2$PNH(C$_6$F$_5$) in 25 ml dry toluene and stirred for 1 hour at room temperature. To the resulting mixture 286 mg (1.64 mmol) (o-phenylenedioxy)PCl in 10 ml toluene was slowly added and allowed to stir for 1 hour at room temperature. The precipitate was removed by centrifugation. The solvent was removed in vacuo. Pentane was added (about 10 ml) yielding a clear solution. From this solution (2-methoxyphenyl)$_2$PN(C$_6$F$_5$)(o-phenylenedioxy) precipitated in several fractions. $^{31}$P-NMR (in C$_6$D$_6$) δ 138.4 and 51.3 (J$_{PP}$=16 HZ). $^{19}$F-NMR (in C$_6$D$_6$) δ −143 (o); −164.1 (m); −157.1 (p).

Ligand Composition H" (Comparative)

The (o-phenylenedioxy)PN(methyl)P(o-phenylenedioxy) ligand composition was prepared by analogy to the method reported for the preparation of (o-phenylenedioxy)PN(isopropyl)P(o-phenylenedioxy) in Heteroatom Chem. Vol. 2, 477 (1991).

Under a nitrogen atmosphere 1 ml methylamine (2 M in THF) was added to 5 ml dry toluene. This solution was cooled to −20° C. At this temperature slowly 150 mg (o-phenylenedioxy)PCl in 1 ml toluene was slowly added. After several days 87 mg Et$_3$N in 5 ml pentane was added. The precipitate was removed by centrifugation. The solvents were removed under vacuum. Yielding (o-phenylenedioxy)PNH(methyl) contaminated with a small amount of toluene. $^{31}$P-NMR (in C$_6$D$_6$) δ 143.9.

To 30 mg (o-phenylenedioxy)PNH(methyl) in 1 ml C$_6$D$_6$ was added 30 mg triethylamine and 30 mg (o-phenylenedioxy)PCl. An instantaneous reaction was observed by $^{31}$P-NMR. Finally 2 ml of pentane was added. The precipitate was removed by centrifugation. The solvents were removed under vacuum. The final product was isolated as a white solid. $^{31}$P-NMR (in C$_6$D$_6$) δ 142.0.

Ligand Composition K" (Comparative)

The (2-methoxyphenyl)$_2$PN(CH$_3$)P(2-methoxyphenyl)$_2$ ligand was prepared by first forming a solution of 1.59 g (5 mmol) (2-methoxyphenyl)$_2$PNEt$_2$ in 20 ml diethyl ether. To this solution 10 ml of a 1 M HCl solution in diethyl ether (10 mmol HCl) was added under an inert atmosphere at room temperature. The suspension thus formed was stirred overnight. The diethyl ether was removed from the product under vacuum and 20 ml of dry toluene was added. The resulting solution was filtered and the toluene was removed from the filtrate under vacuum to yield a white solid (2-methoxyphenyl)$_2$PCl product.

A solution of 0.51 g (5 mmol) of triethylamine in 20 ml of dry dichloromethane was added to the (2-methoxyphenyl)$_2$PCl product. To the resulting mixture, 1.25 ml of a 2 M H$_2$NMe solution in THF (2.5 mmol) was added and allowed to stir overnight. The solvents were removed from the resulting solution in vacuo and 20 ml of dry toluene was added. The mixture was then filtered.

The toluene was removed from the filtrate under vacuum, and 10 ml of methanol was added to the residue to produce a suspension, which was filtered once more, to leave the solid white (2-methoxyphenyl)$_2$PN(CH$_3$)P(2-methoxyphenyl)$_2$ product which was isolated.

Ligand Composition L (Comparative)

The reaction product of (2-methoxyphenyl)$_2$PNH(isopropyl) and (2-methoxyphenyl)$_2$PCl (ligand composition L) was prepared as follows.

Under a nitrogen atmosphere, 3 ml triethylamine was added to 1.5 ml isopropylamine (17.6 mmol) in 5 ml dry toluene. To the resulting mixture, 2.2 g (7.84 mmol) (2-methoxyphenyl)$_2$PCl in 20 ml toluene was slowly added and allowed to stir overnight at room temperature. The precipitate was removed by centrifugation. The solvents were removed from the resulting solution in vacuo. Washing with pentane yielded (2-methoxyphenyl)$_2$PNH(isopropyl) as a white solid. $^{31}$P-NMR (in C$_6$D$_6$) δ 21.8.

Under a nitrogen atmosphere, 80 mg (1.0 mmol) of neopentyl lithium was slowly added to 300 mg (0.99 mmol) of (2-methoxyphenyl)$_2$PNH(isopropyl) in 30 ml dry toluene. To the resulting mixture 277 mg (0.99 mmol) (2-methoxyphenyl)$_2$PCl was slowly added. The mixture was stirred overnight at room temperature. The precipitate was removed by centrifugation. The solvent was removed in vacuo. The residue was washed with pentane. The product has according to $^{31}$P-NMR at least predominantly the P—P=N(isopropyl) structure, i.e. (2-methoxyphenyl)$_2$P(2-methoxyphenyl)$_2$PN (isopropyl), and was used without further purification. $^{31}$P-NMR (in C$_6$D$_6$) δ 0.0 and −35.4 (J$_{PP}$=258 Hz).

Ligand Composition M" (Comparative)

The (phenyl)$_2$PN(isopropyl)P(phenyl)$_2$ ligand was prepared by the following method. At 0° C., under a nitrogen atmosphere, 15 ml triethylamine was added to 6.3 g (phenyl)$_2$PCl in 80 ml of dry dichloromethane. To the resulting mixture, 0.844 g isopropylamine was added and allowed to stir overnight at room temperature. The solvents were removed from the resulting solution in-vacuo and 50 ml of dry toluene was added. The mixture was then filtered over a small layer of silica. The toluene was removed from the filtrate under vacuum, (phenyl)$_2$PN(isopropyl)P(phenyl)$_2$ product was isolated as a white solid. Crystallization from ethanol yielded (phenyl)$_2$PN(isopropyl)P(phenyl)$_2$ as white crystals.

Ligand Component N" [Used in the In Situ Preparation of Ligand Composition C']

The (phenyl)$_2$PN(isopropyl)P(2-methoxyphenyl)$_2$ ligand was prepared by the following method.

Under a nitrogen atmosphere, 12 ml triethylamine was added to 3.39 g isopropylamine in 10 ml dry toluene. To the resulting mixture, 5.15 ml (phenyl)$_2$PCl was slowly added and allowed to stir overnight at room temperature. The precipitate was removed by filtration. The solvents were removed from the resulting solution in vacuo. To the evaporation residue pentane was added and subsequently the solvent was removed in vacuo from the pentane solution, yielding (phenyl)$_2$PNH(isopropyl) as a colourless oil, which crystallized on standing at room temperature.

Under a nitrogen atmosphere, 3 ml triethyl amine was added to 0.9 g of the isolated (phenyl)$_2$PNH(isopropyl) in 5 ml of dry dichloromethane. To the resulting mixture, 1.1 g (2-methoxyphenyl)$_2$PCl was added and allowed to stir for a week at room temperature. To the resulting reaction mixture 5-10 ml of dry toluene was added. The precipitate was removed by centrifugation. The solvents were removed from the resulting solution in vacuo. The resulting mixture was first washed with pentane and thereupon stirred with methanol yielding a white solid. The white solid was washed with pentane and dried in vacuo. Yield 0.7 g of (phenyl)$_2$PN(isopropyl)P(2-methoxyphenyl)$_2$. $^{31}$P-NMR (in C$_6$D$_6$) broad signals δ 55.9 and 24.8.

Ligand Component Q [Used in the In Situ Preparation of Ligand Composition T']

The racemic phosphorus derivative of rac-2,2' dihydroxy-1,1'-binaphthyl, (Rac-1,1'-binaphthyl-2,2'-dioxy)PCl, also called (rac-1,1'-binaphthalene-2,2'-dioxy)PCl, rac-1,1'-binaphthyl-2,2' phosphorochloriditie or (rac-O,O-binaphtholato)PCl was prepared from phosphorus trichloride and rac-2,2'-dihydroxy-1,1'-binaphthyl (purchased from Aldrich) according to the method reported by N. Greene and T. P. Kee, Synthetic Communications 23 (1993) 1651. The product showed in $^{31}$P-NMR (in C$_6$D$_6$) a signal at δ 179.5 (δ$_P$ 178.8 (s) according to the above-mentioned literature).

Ligand Composition T'

The reaction product of (2-methoxyphenyl)$_2$PN(methyl)P (2-methoxyphenyl)$_2$ and (rac-1,1'-binaphthyl-2,2'-dioxy)PCl (ligand composition T') was prepared as follows.

In a NMR-tube under a nitrogen atmosphere 14 mg (40 mmol) (rac-1,1'-binaphthyl-2,2'-dioxy)PCl was added to 22 mg (36 mmol) (2-methoxyphenyl)$_2$PN(methyl)P(2-methoxyphenyl)$_2$ in 1 ml dry d8-toluene. This mixture was heated in an oil bath of 110° C. for 40 hours. According to $^{31}$P-NMR spectroscopy, the product was an approximately 1 to 1 (mol/mol) mixture of (2-methoxyphenyl)$_2$PCl and predominantly a P—P=N(methyl) structure with on one P atom the rac-1,1'-binaphthyl-2,2'-dioxy group and on the other P atom two 2-methoxyphenyl groups (either (rac-1,1'-binaphthyl-2,2'-dioxy)P(2-methoxyphenyl)$_2$PN(methyl) or (2-methoxyphenyl)$_2$P(rac-1,1'-binaphthyl-2,2'-dioxy)PN(methyl))(see Scheme 1). $^{31}$P-NMR (in C$_7$D$_8$) δ 151.3 and 35.1 (J$_{PP}$=385 Hz). This mixture was used as such in the catalyst for ethylene oligomerization experiments without further purification.

Scheme 1: in situ preparation of ligand composition T'

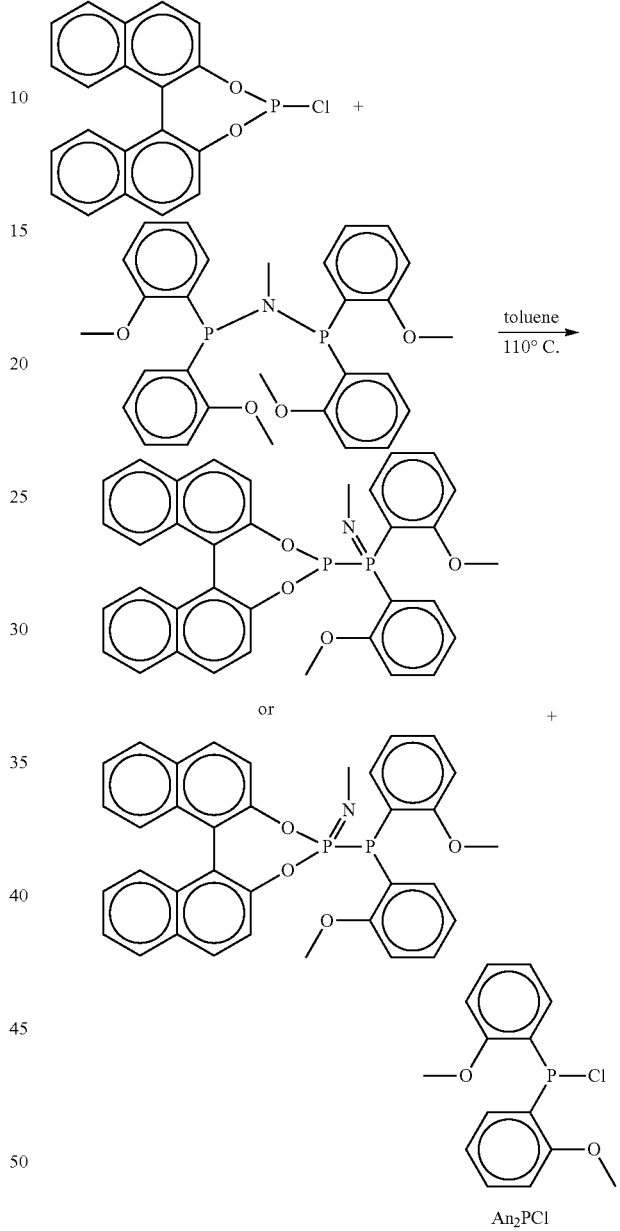

Ligand Component U

The preparation of N-methylnaphto[1,8-de][1,3,2]dioxaphosphinine-2-amine (see Scheme 2).

Scheme 2

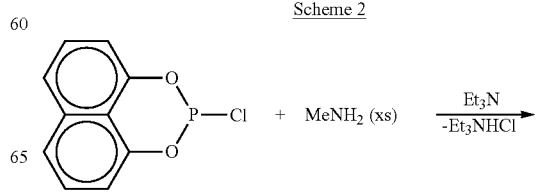

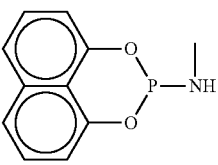

Under a nitrogen atmosphere, 0.4 ml triethylamine was added to 1.5 ml methylamine (2 M in THF) in 20 ml dry toluene. To the resulting solution was cooled to 5° C. and 250 mg 2-chloronaphtho[1,8-de][1,3,2]dioxaphosphinine (available from Hansa Fine Chemicals GmbH, Bremen, Germany) was slowly added. After stirring overnight at room temperature 20 ml hexane was added. The precipitate was removed by centrifugation. The solvents were removed under vacuum. The product N-methylnaphtho[1,8-de][1,3,2]dioxaphosphinine-2-amine was isolated as an oil and used as such. $^{31}$P-NMR $C_6D_6$ δ 121.2.

Ligand Composition V

The reaction product of N-methylnaphtho[1,8-de][1,3,2] dioxaphosphinine-2-amine and (2-methoxyphenyl)$_2$PCl (ligand composition V, see Scheme 3) was prepared as follows.

Scheme 3

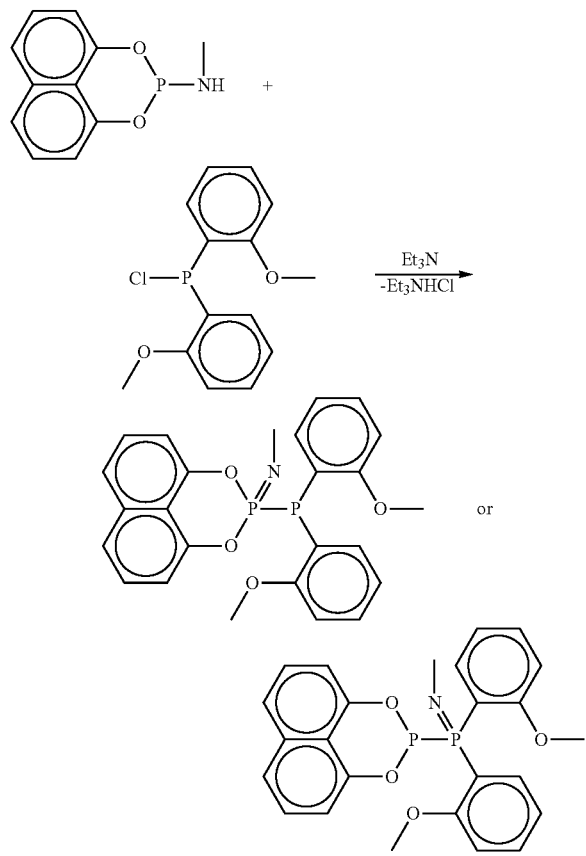

Under a nitrogen atmosphere, 350 mg triethylamine was added to 150 mg N-methylnaphtho[1,8-de][1,3,2]dioxaphosphinine-2-amine 20 ml dry toluene. To the resulting solution, 230 mg (2-methoxyphenyl)$_2$PCl was slowly added and allowed to stir overnight at room temperature. To the resulting mixture hexane was added. The precipitate was removed by centrifugation. The solvents were removed under vacuum. The product was crystallized from a hexane/toluene mixture (−20° C.) and isolated as a white solid. $^{31}$P-NMR $C_6D_6$ δ 130.6 and 36.3 ($J_{PP}$=370 Hz).

Co-Catalyst

The co-catalyst used in the experiments below was selected from:

Methyl aluminoxane (MAO) in toluene, [Al]=5.20% wt, supplied by Crompton GmbH, Bergkamen, Germany;

Examples 1-31

Catalyst System Preparation for Simultaneous Trimerization and Tetramerization in a Batch Autoclave In a Braun MB 200-G dry box the chromium tris(acetylacetonate) (typically about 30 μmol) and the ligand component, as indicated in Table 1, were placed in a glass bottle. Dry toluene (typically 4 g) was added to the glass bottle to obtain a catalyst precursor solution. Finally, the bottle was sealed by a septum cap.

The solution or part of the solution was used in the oligomerisation reaction of ethylene.

Oligomerisation Reactions of Ethylene in a 1.0-Liter Batch Autoclave

Oligomerisation experiments were performed in a 1.0-liter steel autoclave equipped with jacket cooling with a heating/cooling bath (ex. Julabo, model ATS-2) and a turbine/gas stirrer and baffles.

The reactor was scavenged by introducing 250 ml toluene, MAO (0.6 g solution) and subsequent stirring at 70° C. under nitrogen pressure of 0.4-0.5 MPa for 30 min. The reactor contents were discharged via a tap in the base of the autoclave. The reactor was evacuated to about 0.4 kPa and loaded with approximately 250 ml toluene, heated to 40° C. and pressurised with ethylene to 15 barg.

Whilst stirring, an MAO-solution (typically an intake of 3.12 g, 6 mmol Al, to attain an Al/Cr atomic ratio of 200) was added to the reactor with the aid of toluene (the total volume injected was about 25 ml: the MAO-solution diluted with toluene to 8 ml was injected and the injector system was rinsed twice with 8 ml toluene) and the stirring at 800 rpm was continued for 30 minutes.

The Cr-catalyst precursor, prepared as described above, was introduced into the stirred reactor using an injection system with the aid of toluene (the total volume injected was about 25 ml: the catalyst solution diluted with toluene to 8 ml was injected and the injector system was rinsed twice with 8 ml toluene). The initial loading of the reactor was about 300 ml of largely toluene.

The addition of the catalyst system resulted, after an initial induction period of about 5 minutes, in an exotherm (generally 5-10° C.), which typically reached a maximum within 1 minute and was followed by establishment of the temperature and pressure indicated in Table 1.

After consuming the desired volume of ethylene, the reaction was stopped by rapid cooling to room temperature (about 5 minutes), followed by venting of the ethylene, and decanting the product mixture into a collection bottle using a tap in the base of the autoclave. Exposure of the mixture to air resulted in rapid deactivation of the catalyst.

After addition of n-hexylbenzene, (0.5-3.5 g) as an internal standard, to the crude product, the amount of the $C_4$-$C_{30}$ olefins and purity of $C_6$, $C_8$ and $C_{10}$ olefins was determined by gas chromatography. The experimental data is reported in Table 1.

In the case of experiments under 30, 40 or 50 barg of ethylene pressure, a similarly equipped 0.5-liter steel autoclave has been used, loaded (in the same manner as the above-described procedure for the 1.0-liter autoclave) with half the amounts of the components used in the corresponding 1.0-liter experiments to maintain the same Al/Cr atomic ratio (of about 200) and final alpha olefin concentration as much as practicable.

The experimental data is provided in Table 1 below.

TABLE 1

The performance of $R^a{}_2P—P(R^c)_2=N—R^b$, $R^b—N=P(R^a)_2PR^c{}_2$ and/or $R^a{}_2P—N(R^b)—PR^c{}_2$ ligands in Cr-catalyzed ethylene oligomerization

| Example | Cr (μmol) | Ligand (mol$_{lig}$)/(mol$_{Cr}$) | Co-Catalyst | Temperature (Initial Temp) (° C.) | Pressure (barg) | Time (min) | TOF (TON) ‡ | $C_6$ (% wt) | 1-$C_6$* (% wt) |
|---|---|---|---|---|---|---|---|---|---|
| 1 | 32 | A (1.1) | MAO | 70 (40) | 15 | 30 | 130 (65) | 53.6 | 97.7 |
| 2 | 15 | A (1.1) | MAO | 70 (40) | 30 | 72 | 246 (295) | 49.6 | 97.7 |
| 3 | 14 | A (1.1) | MAO | 85 (40) | 30 | 35 | 415 (242) | 51.1 | 97.4 |
| 4 | 15 | A (2.3) | MAO | 85 (40) | 30 | 40 | 343 (229) | 50.6 | 97.4 |
| 5 | 3 | A (1.1) | MAO | 100 (40) | 50 | 60 | 594 (594) | 50.1 | 97.6 |
| 6 | 3 | A (2.3) | MAO | 100 (40) | 50 | 90 | 365 (547) | 52.4 | 97.4 |
| 7 | 30 | A' (1.1) | MAO | 70 (40) | 15 | 60 ## | 76 (76) | 45.1 | 97.2 |
| 8 | 15 | A' (1.2) | MAO | 70 (70) | 30 | 38 | 139 (88) | 33.4 | 96.7 |
| 9 | 20 | A' (1.2) | MAO | 85 (70) | 30 | 43 | 69 (49) | 45.3 | 97.1 |
| 10 | 30 | B' (1.1) | MAO | 70 (40) | 15 | 225 ## | 20 (76) | 57.2 | 94.1 |
| 11 | 15 | B' (1.1) | MAO | 70 (70) | 30 | 94 | 48 (75) | 45.5 | 92.0 |
| 12 | 15 | C" (1.1) | MAO | 70 (70) | 30 | 19 | 317 (100) | 50.8 | 98.6 |
| 13 | 15 | C" (2.4) | MAO | 85 (40) | 30 | 80 | 185 (246) | 59.8 | 98.2 |
| 14 | 3 | C" (2.4) | MAO | 100 (40) | 50 | 80 | 643 (858) | 64.9 | 98.1 |
| 15 # | 15 | D" (1.3) | MAO | 70 (40) | 30 | 30 | 7 (4) | 29.6 | 71.6 |
| 16 | 15 | E (1.1) | MAO | 70 (40) | 30 | 30 | 9 (4) | 10.6 | 66.4 |
| 17 | 30 | F (1.1) | MAO | 70 (40) | 15 | 85 | 78 (111) | 38.8 | 98.8 |
| 18 | 15 | F (1.1) | MAO | 70 (40) | 30 | 37 | 270 (167) | 44.7 | 99.0 |
| 19 | 16 | F (2.3) | MAO | 85 (40) | 30 | 35 | 269 (157) | 33.6 | 98.7 |
| 20 | 3 | F (2.3) | MAO | 100 (40) | 50 | 60 | 181 (181) | 40.8 | 98.8 |
| 21 | 15 | G" (1.3) | MAO | 70 (70) | 30 | 35 | 5 (3) | 58.9 | 97.8 |
| 22 | 17 | G" (2.4) | MAO | 120 (40) | 50 | 85 | 5 (8) | 16.0 | 95.8 |
| 23 # | 15 | H" (0.9) | MAO | 70 (40) | 30 | 75 | 2 (3) | 26.4 | 93.6 |
| 24 # | 15 | K" (1.1) | MAO | 70 (40) | 30 | 36 | 705 (423) | 85.0 | 97.5 |
| 25 # | 16 | L (1.5) | MAO | 70 (70) | 30 | 20 | 5 (2) | 82.5 | 100.0 |
| 26 # | 15 | M" (1.1) | MAO | 40 (40) | 30 | 33 | 203 (113) | 17.4 | 68.5 |
| 27 # | 15 | M" (1.1) | MAO | 80 (80) | 30 | 30 | 26 (13) | 20.3 | 92.8 |
| 28 | 15 | T' (1.1) | MAO | 70 (70) | 30 | 32 | 148 (79) | 42.5 | 97.6 |
| 29 | 15 | T' (1.1) | MAO | 85 (85) | 30 | 37 | 137 (84) | 49.2 | 97.3 |
| 30 | 15 | T' (1.1) | MAO | 85 (85) | 40 | 30 | 183 (92) | 44.0 | 97.1 |
| 31 | 15 | V (1.2) | MAO | 70 (70) | 30 | 21 | 174 (61) | 32.5 | 96.5 |

| Example | $C_8$ (% wt) | 1-$C_8$** (% wt) | $C_{10}$† (% wt) | $C_{12}$-$C_{14}$† (% wt) | Solids (% wt) | Total product (g) | 1-$C_6$ + 1-$C_8$ on Total Product (% wt) |
|---|---|---|---|---|---|---|---|
| 1 | 35.9 | 98.4 | 3.4 | 4.6 | 0.05 | 54.6 | 87.7 |
| 2 | 38.2 | 98.5 | 4.1 | 4.6 | 0.02 | 124.3 | 86.1 |
| 3 | 37.2 | 98.3 | 3.6 | 4.4 | 1.5 | 95.8 | 86.4 |
| 4 | 38.5 | 98.3 | 3.4 | 4.4 | 1.0 | 96.1 | 87.2 |
| 5 | 32.2 | 98.3 | 2.9 | 2.4 | 10.3 | 49.8 | 80.5 |
| 6 | 38.5 | 98.3 | 2.6 | 2.8 | 1.4 | 45.7 | 88.9 |
| 7 | 44.6 | 98.5 | 2.4 | 4.4 | 0.05 | 64.8 | 87.8 |
| 8 | 52.7 | 98.5 | 2.0 | 4.4 | 1.3 | 37.2 | 84.1 |
| 9 | 43.1 | 98.2 | 2.1 | 3.4 | 1.7 | 28.1 | 86.3 |
| 10 | 31.7 | 97.2 | 4.3 | 4.3 | 0.08 | 62.8 | 84.6 |
| 11 | 43.6 | 96.8 | 3.5 | 4.6 | 0.5 | 31.5 | 84.1 |
| 12 | 34.2 | 98.8 | 8.1 | 6.8 | 0.07 | 43.5 | 83.8 |
| 13 | 22.6 | 98.4 | 10.3 | 5.7 | 0.6 | 103.1 | 81.0 |
| 14 | 21.1 | 98.3 | 8.6 | 3.9 | 1.0 | 71.6 | 84.3 |
| 15 # | 60.8 | 97.1 | 2.1 | 2.2 | 2.7 | 1.5 | 80.2 |
| 16 | 21.6 | 92.6 | 5.5 †† | 7.5 | 43.4 | 1.8 | 27.0 |
| 17 | 25.7 | 99.2 | 5.4 | 5.5 | 19.3 | 93.4 | 63.9 |
| 18 | 39.0 | 99.5 | 5.2 | 6.0 | 3.7 | 69.8 | 83.0 |
| 19 | 24.9 | 99.2 | 3.7 | 4.7 | 25.0 | 70.0 | 57.9 |
| 20 | 26.8 | 99.3 | 3.0 | 3.5 | 19.7 | 15.2 | 66.9 |
| 21 | 12.4 | 95.5 | 4.5 | 4.5 | 18.6 | 1.2 | 69.4 |
| 22 | 4.7 | 91.8 | 2.1 | 2.9 | 65.1 | 3.6 | 19.6 |
| 23 # | 24.6 | 96.1 | 10.9 †† | 14.3 | 7.7 | 1.3 | 48.3 |
| 24 # | 4.1 | 99.8 | 10.0 | 0.9 | 0.02 | 177.6 | 87.0 |
| 25 # | 3.6 | 93.0 | 3.0 | 3.1 | 7.2 | 0.7 | 85.8 |
| 26 # | 70.2 | 98.8 | 1.8 †† | 4.4 | 0.5 | 47.2 | 81.3 |
| 27 # | 25.9 | 94.4 | 2.3 †† | 3.7 | 47.4 | 5.5 | 43.3 |
| 28 | 48.3 | 98.6 | 1.9 | 3.1 | 0.06 | 33.9 | 89.1 |
| 29 | 43.8 | 98.4 | 2.1 | 2.8 | 0.06 | 35.2 | 90.9 |

TABLE 1-continued

The performance of $R^a{}_2P-P(R^c)_2=N-R^b$, $R^b-N=P(R^a)_2PR^c{}_2$ and/or
$R^a{}_2P-N(R^b)-PR^c{}_2$ ligands in Cr-catalyzed ethylene oligomerization

| 30 | 47.8 | 98.5 | 1.9 | 2.9 | 0.05 | 38.7 | 89.8 |
| 31 | 53.8 | 98.6 | 1.8 | 3.4 | 3.5 | 25.4 | 84.4 |

The following equilibria are assumed in the presence of activated chromium:

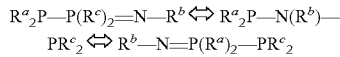

A $R^a{}_2$=o-phenylenedioxy, $R^b$=methyl, $R^c$=o-methoxyphenyl (A: ligand predominantly in either of the P—P═N forms).

A' $R^a{}_2$=o-phenylenedioxy, $R^b$=methyl, $R^c$=o-methoxyphenyl (A': in-situ prepared ligand A; containing about 1 mol/mol (o-methoxyphenyl)$_2$P—Cl).

B' $R^a{}_2$=o-phenylenedioxy, $R^b$=methyl, $R^c{}_2$=o-methylphenyl+phenyl (B': in-situ prepared ligand B, predominantly in either of the P—P═N forms; containing about 1 mol/mol (o-methoxyphenyl)(phenyl)P—Cl).

C" $R^a{}_2$=o-phenylenedioxy, $R^b$=isopropyl, $R^c$=o-methoxyphenyl (C": ligand predominantly in the P—NP form).

D" $R^a{}_2$=o-phenylenedioxy, $R^b$=isopropyl, $R^c$=phenyl (D": ligand predominantly in the P—N—P form).

E $R^a{}_2$=o-phenylenedioxy, $R^b$=methyl, $R^c$=phenyl (E: ligand predominantly in either of the P—P═N forms).

F $R^a{}_2$=o-phenylenedioxy, $R^b$=methyl, $R^c$=tert-butyl (F: ligand predominantly in either of the P—P═N forms).

G" $R^a{}_2$=o-phenylenedioxy, $R^b$=pentafluorophenyl, $R^c$=o-methoxyphenyl (G": ligand predominantly in the P—NP form).

H" $R^a{}_2$=o-phenylenedioxy, $R^b$=methyl, $R^c{}_2$=o-phenylenedioxy (H": ligand predominantly in the P—N—P form).

K" $R^a$=o-methoxyphenyl, $R^b$=methyl, $R^c$=o-methoxyphenyl (K": ligand predominantly in the P—N—P form).

L $R^a$=o-methoxyphenyl, $R^b$=isopropyl, $R^c$=o-methoxyphenyl (L: ligand predominantly in either of the P—P═N forms).

M" $R^a$=phenyl, $R^b$=isopropyl, $R^c$=phenyl (M": ligand predominantly in the P—N—P form).

T' $R^a{}_2$=rac-1,1'-binaphthyl-2,2'-dioxy, $R^b$=methyl, $R^c$=o-methoxyphenyl (T': in-situ prepared T, predominantly in either of the P—P═N forms; containing about 1 mol/mol (o-methoxyphenyl)$_2$P—Cl).

V $R^a2$=1,8-naphthalenedioxy, $R^b$=methyl, $R^c$=o-methoxyphenyl (V: ligand predominantly in either of the P—P═N forms).

πComparative example.
During 30 minutes at 40° C.
‡ Turnover frequency (TOF) in hourly kmol converted ethylene/mol catalyst (kmol/mol*h); turnover number (TON) in kmol converted ethylene/mol catalyst (kmol/mol).
*Percentage (%) of 1-hexene by weight of the $C_6$ portion of the product composition.
** Percentage (%) of 1-octene by weight of the $C_8$ portion of the product composition.
† Predominantly branched and/or internal olefins, unless indicated differently.
†† Equal or larger than 50% of 1-decene by weight of the $C_{10}$ portion of the product composition.
$C_6$ Hydrocarbons containing 6 carbon atoms; 1-$C_6$ is 1-hexene.
$C_8$ Hydrocarbons containing 8 carbon atoms; 1-$C_8$ is 1-octene.
$C_{10}$ Hydrocarbons containing 10 carbon atoms.
$C_{12}$-$C_{14}$ Hydrocarbons containing 12 and/or 14 carbon atoms.
Solids: The amount of wax and polyethylene isolated by filtration.
Total product: The amount of $C_4$-$C_{100}$ olefins, derived from GC analysis, including the amount of solids.

For economic narrow-cut alpha-olefin production, e.g. the production of a mixture of 1-hexene and 1-octene in a combined overall yield of >80%, preferably in a weight ratio of 20/80 to 80/20, each in >92% selectivity (on total C6 or total C8) in a single plant to enhance the economy of scale a special kind of catalyst is required. At industrially interesting pressures and temperatures of at least 30 barg and 70° C. the comparative catalyst K" and analogous catalyst L predominantly produce 1-hexene and hardly 1-octene. Under these conditions the comparative catalyst M" produces a mixture of hexenes and octenes of low 1-hexene content, but also a large amount of solids at a low TOF. Only at 40° C. comparative catalyst M" produces a mixture of hexenes and octenes of low 1-hexene content at a high TOF.

Surprisingly only the "o-phenylenedioxy-phosphorus" containing catalysts A, A', C", the rac-1,1'-binaphthyl-2,2'-dioxy-phosphorus containing catalyst T' and the 1,8-naphthalenedioxy-phosphorus containing catalyst V and to a less extent B' and F, but remarkably to far less extent, if any, D", E, G", and H", produce mainly 1-hexene and 1-octene in high activities (TOF's) at temperatures of 70° C. and 30 barg. Even at 70-100° C. and 30-50 barg catalysts A, A', C" and T' provide for the selective production of both highly pure 1-hexene and 1-octene in the desired weight ratios with only minor amounts of solids (wax and polyethylene) co-produced. Hence, what is particularly preferred for efficient narrow-cut production of highly pure 1-hexene and 1-octene at industrially interesting rates and temperatures and pressures is a Cr-complex with a PNP structure or its PPN isomers with a methyl or isopropyl group on N, one cyclic alkylenedioxy or arylenedioxy group, preferably one—optionally mono-tetra alkylated—o-phenylenedioxy (catechol) or one—optionally mono-dodeca alkylated—racemic or optically pure 1,1'-binaphthyl-2,2'-dioxy group on one P and at least one o-methoxyphenyl and one phenyl, but preferably two o-methoxyphenyl groups on the other P. If, instead two tert-butyl (also sterically demanding, but electronically different) groups are present on the latter P, generally besides 1-hexene and 1-octene a relatively large (>3.7% wt) amount of solids, mainly wax, is co-produced.

It should be noted that the differences in hexenes/octenes ratios between experiments with ligand A and in-situ prepared ligand A (ligand A') are probably due to the differences in start-up temperature. The activities obtained with the in-situ prepared ligand A' are however invariably lower than those obtained with ligand A, which is ascribed to the presence of (o-methoxyphenyl)$_2$P—Cl.

The invention claimed is:
1. A process for the oligomerisation of olefinic monomers, wherein the process comprises contacting at least one olefinic monomer with a catalyst system catalyst comprising:

a) a source of chromium, molybdenum or tungsten;
b) a ligand having the general formula (IV):

$$(R^8)(R^1)P\text{—}N(R^3)\text{—}P(R^4) \qquad (IV)$$

wherein:
$R^1$ and $R^8$ are both aromatic or heteroaromatic groups which comprise at least one polar substituent group on one of the ortho positions;
the $R^3$ group is selected from hydrogen, a hydrocarbyl group, a substituted hydrocarbyl group, a heterohydrocarbyl group, a substituted heterohydrocarbyl group, a silyl group;
the $R^4$ group is an optionally substituted alkylenedioxy, alkylenedimercapto or alkylenediamino structure which is bound to the phosphorus atom through the two oxygen, sulphur or nitrogen atoms of the alkylenedioxy, alkylenedimercapto or alkylenediamino structure or an optionally substituted arylenedioxy, arylenedimercapto or arylenediamino structure which is bound to the phosphorus atom through the two oxygen, sulphur or nitrogen atoms of the arylenedioxy, arylenedimercapto or arylenediamino structure; and
c) a cocatalyst.

2. A process according to claim 1, wherein the R1 group and the R8 group of the catalyst are both phenyl groups substituted with a polar group on at least one of the ortho positions.

* * * * *